(12) United States Patent
Nan et al.

(10) Patent No.: US 7,838,682 B2
(45) Date of Patent: Nov. 23, 2010

(54) GLUCAGON-LIKE PEPTIDE-1 RECEPTOR AGONISTS, THE PREPARATION AND THE USE OF THE SAME

(75) Inventors: Fajun Nan, Shanghai (CN); Mingwei Wang, Shanghai (CN); Wenlong Wang, Shanghai (CN); Caihong Zhou, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 890 days.

(21) Appl. No.: 10/582,580

(22) PCT Filed: Dec. 25, 2003

(86) PCT No.: PCT/CN03/01115

§ 371 (c)(1),
(2), (4) Date: Jun. 12, 2006

(87) PCT Pub. No.: WO2005/056537

PCT Pub. Date: Jun. 23, 2005

(65) Prior Publication Data

US 2007/0043093 A1    Feb. 22, 2007

(30) Foreign Application Priority Data

Dec. 12, 2003    (CN) .................. 2003 1 0109331

(51) Int. Cl.
C07D 263/08    (2006.01)
A61K 31/42    (2006.01)

(52) U.S. Cl. ...................................... 548/228; 514/376

(58) Field of Classification Search .................. 548/228; 514/376

See application file for complete search history.

(56) References Cited

FOREIGN PATENT DOCUMENTS

| JP | 03-50532 A | 3/1991 |
| JP | 9-244229 A | 9/1997 |
| JP | 11-273865 A | 10/1999 |

OTHER PUBLICATIONS

Okura et al. (STN abstract of WO 95/06032).*
Afifi et al. (Abstract of Revue Roumaine de Chimie (1983), 28(8), 849-55).*
March (March's Advanced Organic Chemistry, 5th ed., (2001) Wiley, 2083 pages).*
Greene et al. (Protective Groups in Organic Synthesis Greene, 3rd ed., New York John Wiley & Sons, Inc., 1999, 779 pages).*
Neye et al. (Abstract of Exp Clin Endocrinol Diabetes. 1998;106(4):292-8).*
Ibrahim, et al. (CAPLUS abstract of: Journal of Chemical Research, Synopses (2002), (2), 60-61, 243-255).*
Shafi, P.M. et al., "A new synthetic route to 4-arylidene-2-phenyl-2-imidazolin-5-ones", Indian J. Chem., Sect. B: Org. Chem. Incl. Med. Chem, 1999, 38B(3), p. 378-379.
Agarwal, Rajesh, et al., "Synthesis of 2-aryl-1-(4morpholinophenyl)-4(3,4-disubstituted-benzylidene)imidazolin-5-ones as CNS active agents", Indian J. Chem., Sect. B, 1983, 22B(3), p. 308-310.

* cited by examiner

*Primary Examiner*—Robert Havlin
(74) *Attorney, Agent, or Firm*—Baker & Hostetler LLP

(57) ABSTRACT

The present invention provides the glucagon-like peptide-1 receptor agonists. It is indicated that the agonists have good binding capability to glucagon-like peptide-1 receptor by pharmacological tests. The present invention also provides the preparation of the agonists.

2 Claims, 1 Drawing Sheet

GLUCAGON-LIKE PEPTIDE-1 RECEPTOR AGONISTS, THE PREPARATION AND THE USE OF THE SAME

CROSS-REFERENCE TO RELATED APPLICATIONS

This application is a National Stage of Patent Cooperation Treaty (PCT) Application No. PCT/CN2003/001115, filed Dec. 25, 2003, entitled, THE GLUCAGON-LIKE PEPTIDE-1 RECEPTOR AGONISTS, THE PREPARATION AND THE USE OF THE SAME, which claims priority to Chinese Patent Application No. 200310109331.0, filed Dec. 12, 2003, all of the disclosure of which are hereby incorporated by reference in their entirety.

FIELD OF THE INVENTION

The present invention relates to a group of glucagon-like peptide-1 receptor (GLP-1 R) agonists. In particularly, the present invention relates to a group of small molecular organic compounds of substituted five-membered heterocyclic ring derivatives which may be used as non-peptide GLP-1 R agonists. The compounds of the present invention may be used as medicaments for treating the glycometabolism disturbance-related diseases such as type II diabetes, insensitivity to insulin and obesity etc. And, the present invention also relates to a process for manufacturing the said GLP-1R agonists.

BACKGROUND OF THE INVENTION

Diabetes mellitus (DM) is a common endocrine metabolic disease with heredity tendency. It is caused mainly by the absolute or relative hyposecretion of the insulin, and it causes metabolic disturbance of saccharide, fat, protein, and subsequently vitamin, water and electrolyte. The manifestations include the increase of glycemia and urine glucose, and the patients have the symptoms of polydipsia, polyphagia, polyuria, dry mouth, and general weakness. The morbidity rate of diabetes mellitus is 1 to 5%, and shows a trend of gradually increasing. Diabetes mellitus, cancer, and cardiovascular diseases are referred as three worldwide serious diseases. The object of treating diabetes mellitus is to correct the disturbance of carbohydrate metabolism, so as to eliminate the symptoms, promote restoration of the function of pancreatic islet, improve the insulin resistance, maintain the better healthy condition and physical strength, and prevent and treat various complications.

Diabetes mellitus is commonly divided into two types: Insulin Dependent Diabetes Mellitus (type I, IDDM) and Non-Insulin Dependent Diabetes Mellitus (type II, NIDDM). Since the pathogenesis for theses two types of diabetes mellitus are different, the medicaments for treating them are far different, which are stated respectively as follows.

Type I diabetes mellitus is caused by virus infection in hereditarily susceptible person which produces the paradoxical reaction of the islet cells through immunoreactions, so that the pancreatic islets begin to be damaged and even lose their function completely. About 5% of diabetes mellitus is type I. At present, the medicaments for treating type I diabetes mellitus mainly include exogenous insulin (including human insulin and animal insulin), drugs having the insulin-like effect, insulin-like growth factor-1 (IGF-1), novel long-acting insulin preparation, and Jin Qi hypoglycemic tablet, etc.

Type II diabetes mellitus is caused by direct impair of β-islet cells which decrease the secretion of insulin. Most of type II diabetes mellitus is caused by a combination of factors that may include genetic traits, life style, environmental contributors, metabolic disorders, obesity, and so on. In this disease state, muscular, hepatic and adipose tissues are insensitive to the insulin, which thereby decrease the intake of the glucose. Most of diabetics suffer from type II diabetes mellitus. At present, the medicaments for the clinical treatment of NIDDM mainly include sulphonylureases, biguanides, other hypoglycemic drugs and adjuvants, etc.

The sulphonylureas hypoglycemic drugs bind to the receptors on the cell membrane of β-islet cells to close the potassium ion channel thereby blocking flowout of potassium ion and inducing depolarization of the cell membrane, so that the calcium ion channels are opened to allow the extracellular calcium ions flow inwardly. The increase of intracellular calcium ions concentration triggers the release of the insulin. Sulphonylureas hypoglycemic drugs can be divided into two generations according to their time of coming into existence. The first generation includes tolpropamide, and the second generation includes glibenclamide (euglucan), gliclazide (diamicron), glipizide and gliquidone etc.

Biguanide hypoglycemic drugs inhibit appetite, improve the binding of insulin to the receptors, promote the anaerobic glycolysis in cells, inhibit tissue respiration and inhibit hepatic gluconeogenesis. The biguanide hypoglycemic drugs mainly include metformin, phenformin and buformin.

Other hypoglycemic drugs mainly include thiazolidinedione drugs (such as troglitazone, rosiglitazone, and pioglitazone, etc), β3-adrenoceptor regulators, glucagon receptor antagonists, fatty acid metabolism interfering agents, α-glycosidase inhibitors (such as acarbose, voglibose, miglitol), and aldose reductase inhibitors, etc.

Recently, the development of research on glycometabolism related endogenous peptide hormone provides a new idea for the treatment of diabetes mellitus. When human body intakes nutrient materials, the enteroendocrine cells release enteropeptide hormone which mainly includes glucagon like peptide-1 (GLP-1) and glucose-dependent insulinotropic peptide (GIP) and regulate metabolism by affecting the insulin generation, gastrointestinal peristalsis, and islet cell proliferation. Wherein, GLP-1 is secreted by entero-pancreatic cells, and activates the adenylate cyclase to synthesize cAMP by highly specifically binding to the GLP-1 receptor of β-islet cells, so as to further activate the protein kinase. The metabolic signal (glycometabolism) and kinase signal (binding of GLP-1) cooperate on the cell membrane level, which finally cause the $Ca^{2+}$ channel to open. The inward flowing of the calcium ions further stimulates the secretion of insulin and inhibits the generation of glucagon, thereby decreases the postprandial blood glucose and maintain blood glucose concentration at a constant level. Also, GLP-1 has the function of neuroregulation, and can retard gastric emptying, and inhibit appetite. All of these are greatly beneficial for the control of diabetes mellitus. Normally, GLP-1 stimulates insulin secretion depending on the blood glucose concentration. As the blood glucose concentration decreases, the effect of GLP-1 on stimulating insulin secretion decreases. Therefore, the action of GLP-1 on decreasing blood glucose is self-limited, and cannot cause hypoglycemia. So, for treating diabetes mellitus, the medicaments with the GLP-1-like action are greatly desirable for the treatment of diabetes mellitus. GLP-1R agonists have been one researching focus of the international drug development organizations. At present, the researches on GLP-1 R mainly focus on the polypeptide regulators. For example, AC 2993 of Amylin Corporation has been applied for clinic test in US (IND). AC2993 is a 39-amino acids polypeptide and has the effect of promoting the secretion of insulin as GLP-1. Since the polypeptide drugs are inconvenient for oral administration and are readily to degrade, non-peptide GLP-1 R regulators are the new researching direction at present.

SUMMARY OF THE INVENTION

The object of the present invention is to design a group of novel small molecular organic compounds of substituted five-membered heterocyclic ring, which may be used as glucagon-like peptide-1 receptor (GLP-1R) agonists, so as to prove a way for searching the lead compounds or the drugs for the medicaments against the diabetes mellitus. Another object of the present invention is to provide a process for preparing these compounds.

The Glucagon-like peptide-1 receptor agonists according the present invention have the specific structural formula as follows:

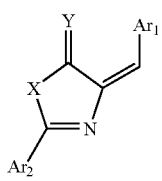

wherein, each of $Ar_1$ and $Ar_2$ independently is phenyl or substituted phenyl, and the substituent groups of the said substituted phenyl is one, two or three groups optionally selected from the following groups: alkyl; hydroxyl; substituted alkoxyl or alkylamino which contains subtitutent groups including halogen, alkoxyl, or hydroxyl; substituted alkanoylxy or alkanoylamino which contains the subtitutent groups including halogen, alkoxyl, or hydroxyl; $C_2$-$C_6$ alkenyl substituted with oxygen or amine, phenyl, benzyl, $C_2$-$C_6$ enoyl, $C_3$-$C_6$ cycloalkanoyl, benzoyl, substituted benzoyl which contains optional one, two, or three substituent groups including alkoxyl and alkylamino, benzyloyl, thenoyl, tert-butoxycarbonyl, adamantane formoxyl

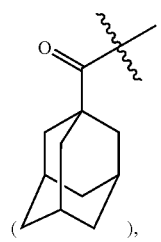

and mandeloyl

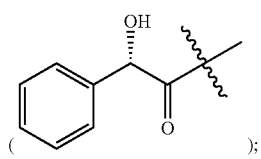

alkoxyl; alkanoylamino; cycloalkoxyl; cycloalkanoylamino; amino; amide; alkoxycarbonyl; cycloalkoxycarbonyl; alkanoylxy; alkanoylamino; cycloalkanoylxy; cycloalkanoylamino; carbamido; urylene; alkanoyl; nitro ; carboxyl; and aldehyde group;

X is O, S, or NH; and

Y is O or S.

When $Ar_1$ is

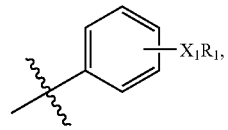

wherein $R_1$ is any one of the following substituent groups: H; alkyl; substituted alkyl which contains substituent groups including halogen, alkoxyl, or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl, or hydroxyl; $C_2$-$C_6$ enoyl; $C_3$-$C_6$ cycloalkanoyl; benzoyl; tert-butoxycarbonyl; substituted benzoyl which contains optional one, two, or three substituent groups including alkoxyl and alkylamino; benzyloyl; thenoyl; adamantane formoxyl; and mandeloyl; and when $X_1$ is O or NH, $Ar_2$ is

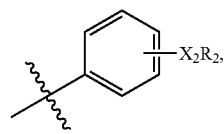

wherein $R_2$ is any one of the following substituent groups: H; alkyl; substituted alkyl which contains substituent groups including halogen, alkoxyl or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl, or hydroxyl; $C_2$-$C_6$ enoyl; $C_3$-$C_6$ cycloalkanoyl; benzoyl; tert-butoxycarbonyl; substituted benzoyl which contains optional one, two or three substituent groups including alkoxyl and alkylamino; benzyloyl; thenoyl; adamantane formoxyl; and mandeloyl; and $X_2$ is O or NH;

or $Ar_2$ is

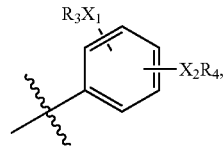

wherein each of $R_3$ and $R_4$ independently is any one of the following substituent groups: H; alkyl; substituted alkyl which contains the substituent groups including halogen, alkoxyl or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl, or hydroxyl; $C_2$-$C_6$ enoyl; $C_3$-$C_6$ cycloalkanoyl; benzoyl; tert-butoxycarbonyl; substituted benzoyl which contains optional one, two or three substituent groups including alkoxyl and alkylamino; benzyloyl; thenoyl; adamantane formoxyl; and mandeloyl; and $X_1$ is O or NH; $X_2$ is O or NH.

When $Ar_1$ is

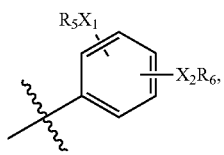

wherein each of $R_5$ and $R_6$ independently is any one of the following substituent groups: H; alkyl; substituted alkyl which contains substituent groups including halogen, alkoxyl, or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl or hydroxyl; $C_2$-$C_6$ enoyl; $C_3$-$C_6$ cycloalkanoyl; benzoyl; substituted benzoyl which contains optional one, two or three substituent groups including alkoxyl and alkylamino; tert-butoxycarbonyl; benzyloyl; thenoyl; adamantane formoxyl; and mandeloyl; when $X_1$ is O or NH; and $X_2$ is O or NH, $Ar_2$ is

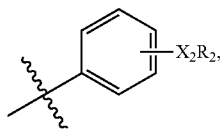

wherein $R_2$ is any one of the following substituent groups: H; alkyl; substituted alkyl which contains substituent groups including halogen, alkoxyl or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl or hydroxyl; $C_2$-$C_6$ enoyl; $C_3$-$C_6$ cycloalkanoyl, benzoyl, substituted benzoyl which contains optional one, two, or three substituent groups including alkoxyl and alkylamino; tert-butoxycarbonyl; benzyloyl; thenoyl; adamantane formoxyl: and mandeloyl; and $X_2$ is O or NH;

or $Ar_2$ is

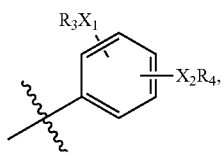

wherein each of $R_3$ and $R_4$ independently is any one of the following substituent groups respectively: H; alkyl; substituted alkyl which contains substituent groups including halogen, alkoxyl or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl, or hydroxyl; $C_2$-$C_6$ enoyl; $C_3$-$C_6$ cycloalkanoyl, benzoyl, substituted benzoyl which contains optional one, two, or three substituent groups including alkoxyl and alkylamino; tert-butoxycarbonyl; benzyloyl; thenoyl; adamantane formoxyl; and mandeloyl; and $X_1$ is O or NH; $X_2$ is O or NH.

The present invention is performed by the following steps. According to the chemical equation:

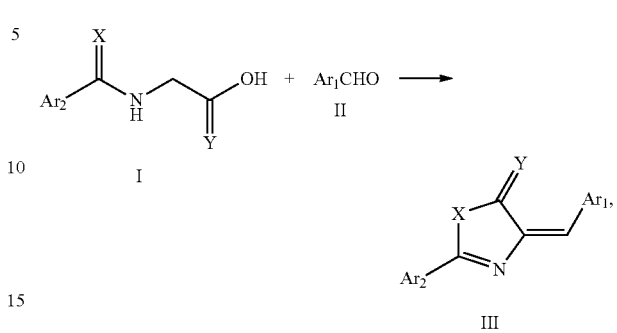

wherein each of $Ar_1$ and $Ar_2$ independently is phenyl or substituted phenyl, and the substituent groups of the said substituted phenyl is one, two or three groups optionally selected from the following group: nitro; carboxyl; aldehyde; tert-butoxycarbonyl and thenoyl substituted with oxygen or amino; X is O, S or NH; and Y is O or S.

Or, according to the following chemical equation:

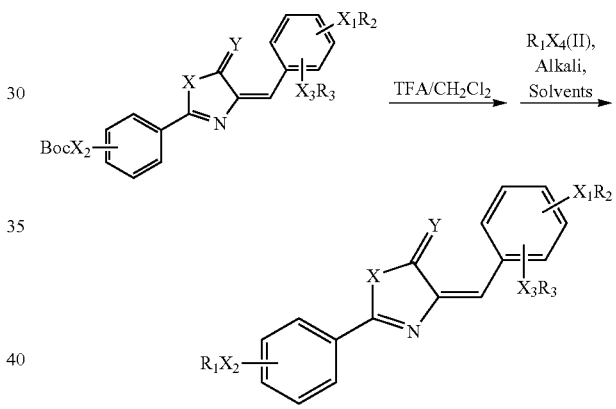

wherein $R_1$, $R_2$ and $R_3$ are optional any one of the following substitutent group: H; alkyl; substituted alkyl which contains substituent groups including halogen, alkoxyl, or hydroxyl; $C_2$-$C_6$ alkenyl; $C_3$-$C_6$ cycloalkyl; phenyl; benzyl; alkanoyl; substituted alkanoyl which contains substituent groups including halogen, alkoxyl, or hydroxyl; $C_2$-$C_6$ enoyl; $C_3$-$C_6$ cycloalkanoyl; benzoyl; tert-butoxycarbonyl; substituted benzoyl which contains optional one, two, or three substituent groups including alkoxyl and alkylamino; benzyloyl; thenoyl; adamantane formoxyl; X is O, S, or NH; Y is O or S; each of $X_1$, $X_2$ and $X_3$ independently is O or NH; and $X_4$ is Cl or OH.

Compound III is produced by the condensation reaction of I and II. And, the condensation is performed in the following solvent: dichloromethane, acetic anhydride, tetrahydrofuran, dimethylfuran, dichloroethane, toluene, benzene, water, dioxane or the mixture of the above solvents. If necessary, some activators may be added into the reaction, such as pyridine, N-methylmorpholine, isobutyl chloroformate, triethylamine, diisopropylethyl amine, or DMAP etc. The reaction temperature is generally −78° C. to the room temperature (for example, for the compound Wang462 etc.), or is 50° to 230° by heating (for example, for the compound Wang520 etc.). The reaction time is different according to the specific reactants. Generally, the reaction process is determined by tracing with TLC. After the completion of the reaction, the general post processing methods include filtrating with a pump, concentrating the reaction solution to remove the solvent, extracting and isolating with column chromatography etc. The final product III is verified with NMR detection.

The process for synthesizing the structural unit of the substituted five-membered heterocyclic ring of the present invention refers to Organic Syntheses, CV 2, 55.

The present invention designs and synthesizes the novel glucagon-like peptide-1 receptor (GLP-1 R) agonists. The GLP-1 R agonists of the present invention bind with the GLP-1 Rand promote the synthesis of cAMP, which may be used to prepare the medicaments for treating the glycometabolism disturbance related diseases such as type II diabetes, insensitivity to insulin and obesity etc. And, the defect of inconvenience for oral administration and being readily to degrade in the prior art, which exists in the medicaments with polypeptide regulators, can be overcame. Furthermore, the compounds of the present invention have relative simple structures and are easy to prepare.

BRIEF DESCRIPTION OF THE DRAWINGS

In FIG. 1, the relative activity of the luciferase induced by 30 nM of positive standard GLP-1 is regarded as 100%.

DETAILED DESCRIPTION

Figure 1:
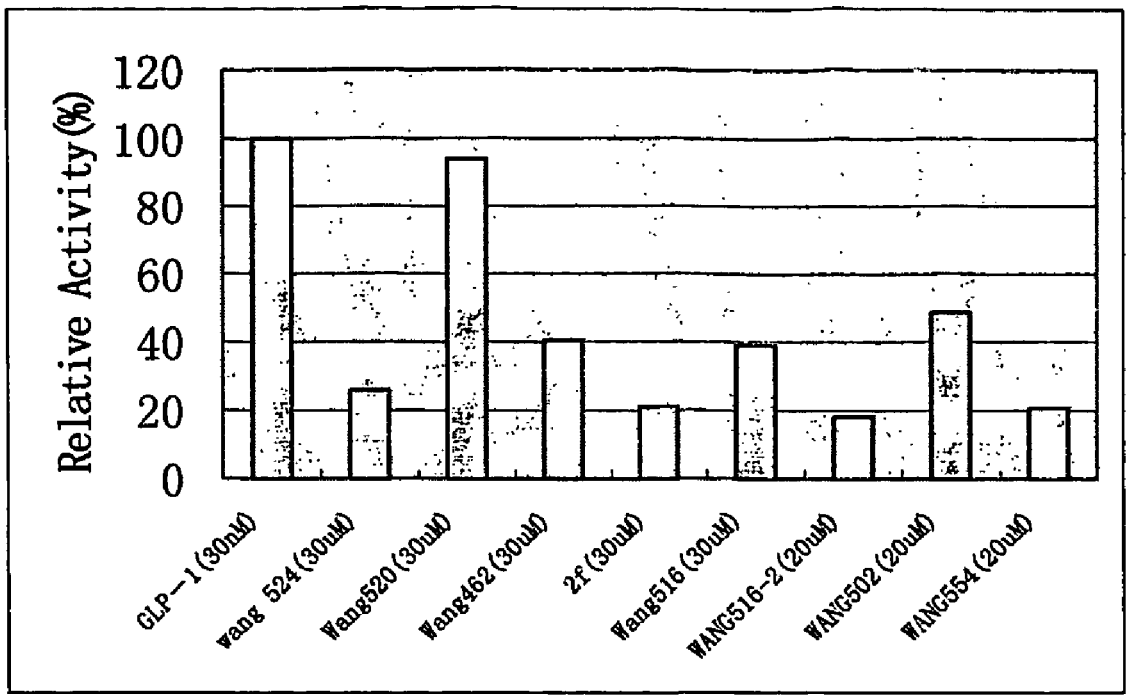
FIG. 1 shows the detecting results of the expression of the report gene for the compounds of the present invention, which is used to evaluate the activating activity of the said compounds on GLP-1R.

The present invention will be further explained with reference to the following specific examples, but they don't limit the present invention in any way.

The preparation process for preparing the compounds in the following preparation examples 1 to 3 mainly includes three reaction operation procedures as follows.

Procedure 1:

Compound I, compound II, sodium acetate and acetic anhydride are mixed and heated to a molten state (ca. 150° to 230°), and maintained for 1 hour. Subsequently, ethanol is added into the reaction mixture and the resulted solution is cooled. The product is separated out after crystallization and filtration. The residual liquid is concentrated to remove the solvents completely, and the product is isolated with column chromatography.

Procedure 2:

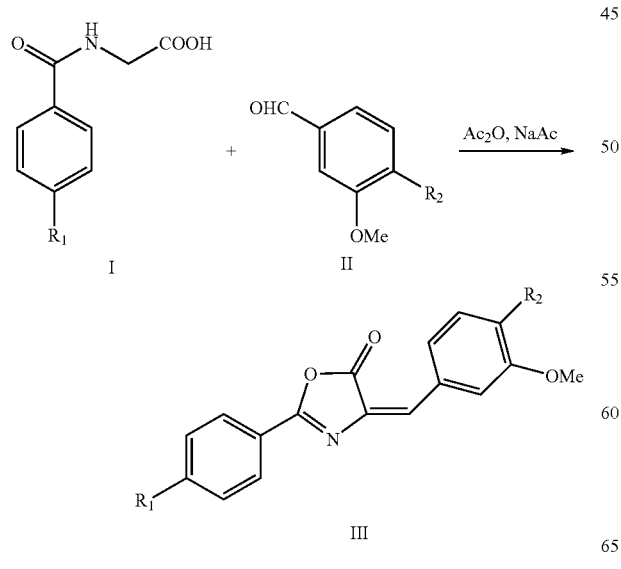

-continued

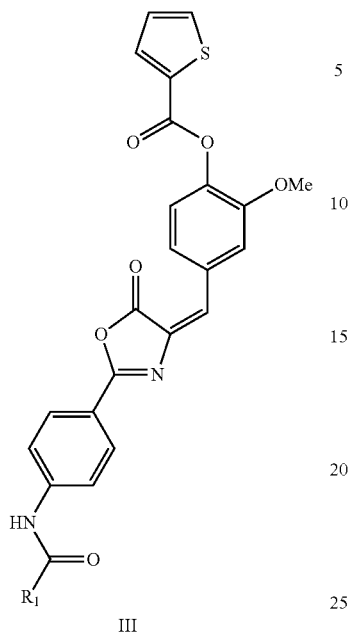

III

The compound I is dissolved in dichloromethane, and cooled in the cryohydrate bath at −20° C., followed by adding trifluoroacetic acid. The solution is stirred at room temperature and traced with TLC until the compound I is reacted completely. After concentrating the reaction system and removing trifluoroacetic acid completely, the substrate is dissolved in dichloromethane, and cooled in the cryohydrate bath at −20°. Then, pyridine and acyl chloride are added orderly. The mixture is stirred at room temperature and traced with TLC. After concentration, the product is isolated with column chromatography.

Procedure 3:

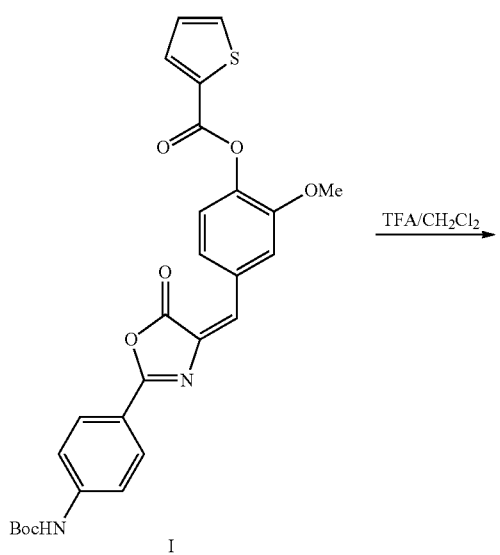

-continued

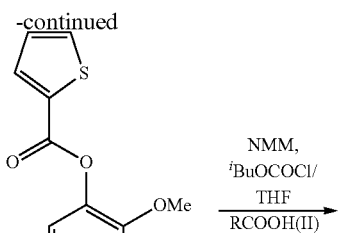

HOOCF$_3$C·H$_2$N

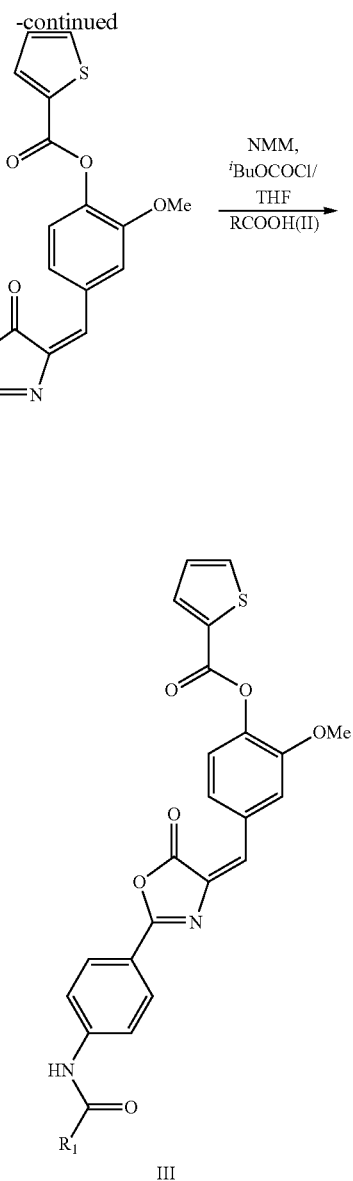

III

The compound I is dissolved in dichloromethane, and cooled in the cryohydrate bath at −20° C., followed by adding trifluoroacetic acid. The solution is stirred at room temperature and traced with TLC until the compound I is reacted completely. The solution is concentrated and trifluoroacetic acid is removed completely. Then, the compound II is dissolved in tetrahydrofuran (THF), and cooled in the cryohydrate bath at −20°. Then, N-methylmorpholine (NMM) and ClCOO$^i$Bu are added orderly. The reaction product of the compound I with trifluoroacetic acid is dissolved in tetrahydrofuran and then transferred into the above mixture with the syringe so as to react at room temperature. The reaction is traced with TLC. After the reaction is completed, the reaction solution is concentrated, and the product is isolated with column chromatography.

For the products, the compounds wang520, wang337, wang405, wang450, wang520-1 and wang462-1 are prepared by the reaction procedure 1, the compounds wang420, wang462, wang524, wang516, wang488, wang568, wang502, wang530, wang504, wang866, 2f, wang582, wang538, and wang496 are prepared by the procedure 2 with the compound wang520, and the compounds wang516-1 and wang591 are prepared by the procedure 3 with the compound wang520.

In the following preparation examples, NMR is measured with Mercury-Vx 300M manufactured by Varian cooperation. NMR criteria are δH/C 7.26/7.77 ppm(CDCl$_3$); δH/C 2.50/39.51 ppm (DSMO-d6); and δH/C 3.31/49.15 ppm (Methyl-d3 Alcohol-d). The agents are provided by Shanghai Chemistry Agents Cooperation. And, the products are purified mainly by the column chromatography. The silica gel for separation is 200-300 mesh, and the model of the silica gel for the column chromatography is thick and hollow (ZLX-II), and is produced by the branch factory of Qingdao Haiyang Chemical plant.

EXAMPLE 1

$^1$H NMR (300 MHz, CDCl$_3$) δ 1.54 (s, 9H), 3.95 (s, 3H), 6.79 (br, 1H), 7.16 (s, 1H), 7.20 (dd, J=4.8 Hz, 3.9 Hz, 1H), 7.25 (d, J=9.9 Hz, 1H), 7.53 (d, J=9.0 Hz, 2H), 7.63 (dd, J=8.4 Hz, 2.1 Hz, 1H), 7.69 (dd, J=4.8 Hz, 1.2 Hz, 1H), 8.02 (dd, J=3.9 Hz, 1.2 Hz, 1H), 8.06 (d, J=8.7 Hz, 2H), 8.17 (d, J=1.5 Hz, 1H); $^{13}$C NMR (75 MHz, CDCl$_3$) δ28.17, 55.79, 81.23, 115.28, 117.92, 119.11, 123.09, 125.74, 128.02, 129.29, 129.41, 132.18, 132.75, 133.29, 133.71, 134.99, 141.57, 143.46, 151.37, 152.08, 159.93, 163.13, 167.46.

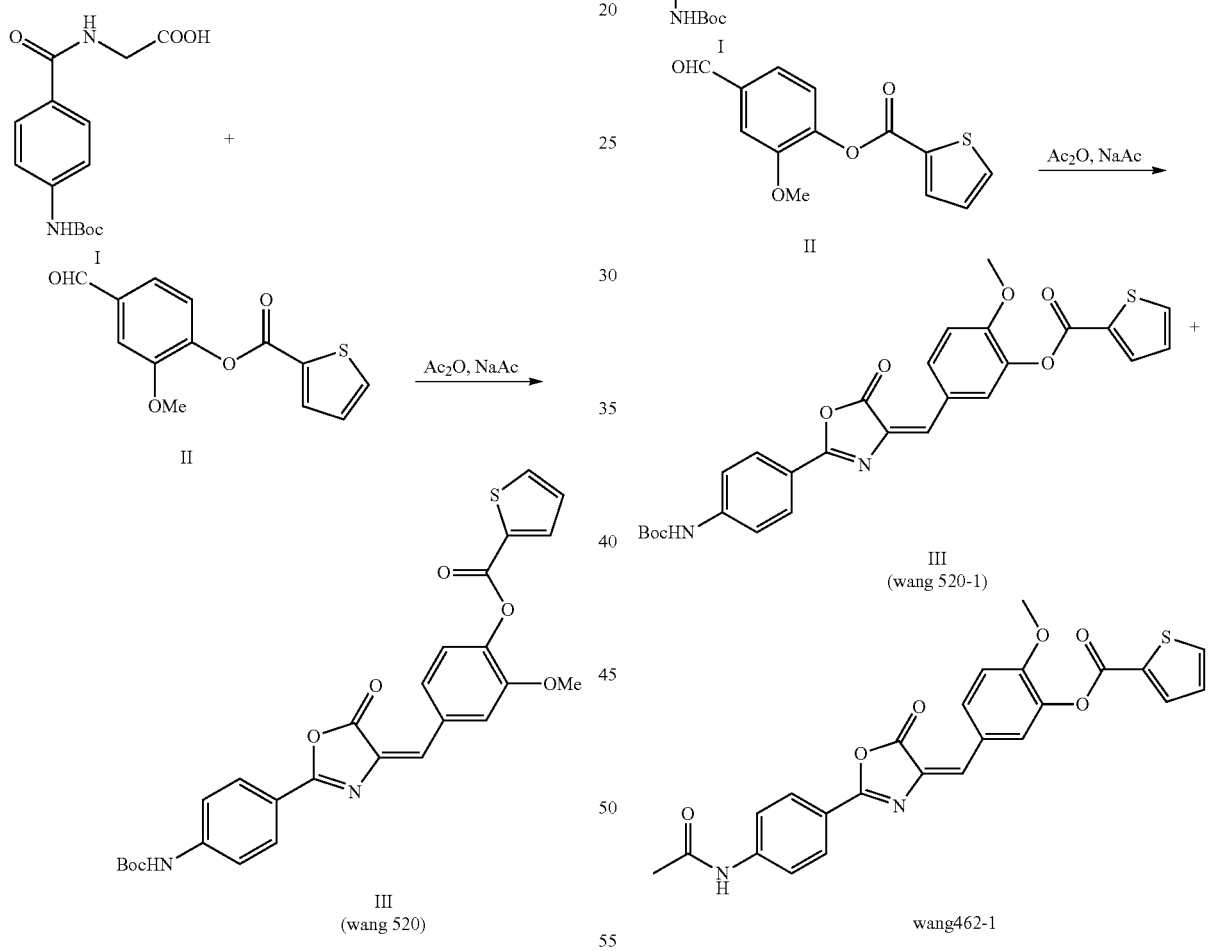

At room temperature, the compound II (466 mg, 1.78 mmol), the compound I (576 mg, 1.96 mmol), sodium acetate (146 mg, 1.78 mmol) and 2 mL of acetic anhydride are mixed and heated to 170° C. The reaction is maintained in the molten state for 1 hour. Then, 2 mL of ethanol is added into the resultant mixture, and the reaction is then cooled to room temperature. Yellow solids are separated out and filtered. The residual liquid is concentrated and the solvent is removed completely to obtain the crude product, which is isolated over silica gel column with petroleum ether/ethyl acetate (5:1 v/v) to obtain 556 mg of the compound wang520 (yield: 60%).

At room temperature, the compound II (466 mg, 1.78 mmol), the compound I (576 mg, 1.96 mmol), sodium acetate (146 mg, 1.78 mmol) and 2 mL of acetic anhydride are mixed and heated to 200° C. The reaction is maintained in the molten state for 1 hour. Then, 2 mL of ethanol is added into the resultant mixture, and then the reaction is cooled to room temperature. The solution is concentrated to obtain the crude product, which is isolated over silica gel column with petroleum ether/ethyl acetate (1:1 v/v) to obtain 158 mg of the compound wang462-1.

¹H NMR (300 MHz, CDCl₃, wang520-1) δ 1.50 (s, 9H), 3.88 (s, 3H), 7.27 (s, 1H), 7.33-7.37 (2H), 7.69 (d, J=8.7 Hz, 2H), 8.01 (d, J=8.7 Hz, 2H), 8.07 (d, J=3.9 Hz, 1H), 8.13 (d, J=4.8 Hz, 1H), 8.22-826 (2H), 9.93 (s, 1H).

¹H NMR (300 MHz, CDCl₃, wang462-1) δ 2.22 (s, 3H), 3.91 (s, 3H), 7.07 (d, J=8.7 Hz, 1H), 7.14 (s, 1H), 7.21 (m, 1H), 7.42 (m, 1H), 7.66 (d, J=8.1 Hz, 2H), 7.71 (d, J=4.8 Hz, 1H), 7.99 (d, J=8.7 Hz, 1H), 8.05 (m, 1H), 8.10 (d, J=8.4 Hz, 2H), 8.19 (m, 1H).

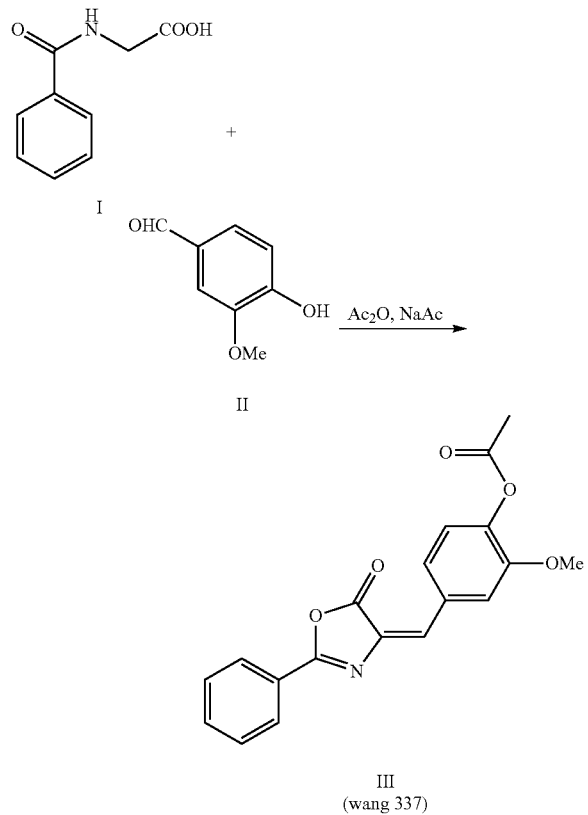

At room temperature, the compound II (1.46 g, 9.6 mmol), the compound I (1.9 g, 10.7 mmol), sodium acetate (0.8 g, 9.8 mmol) and 2.8mL of acetic anhydride are mixed and heated to 170° C. The reaction is maintained in the molten state for 1 hour. Then, 5 mL of ethanol is added into the resultant mixture, and then the reaction is cooled to room temperature. The yellow solids are separated out and filtered to obtain 2.0 g the compound wang337 (yield: 62%).

¹HNMR (300 MHz, CDCl₃) δ 2.35 (s, 3H), 3.97 (s, 3H), 7.13 (d, J=8.4 Hz, 1H), 72.0 (s, 1H), 7.50-7.56 (2H), 7.59-7.65 (2H), 8.12-3.15 (3H).

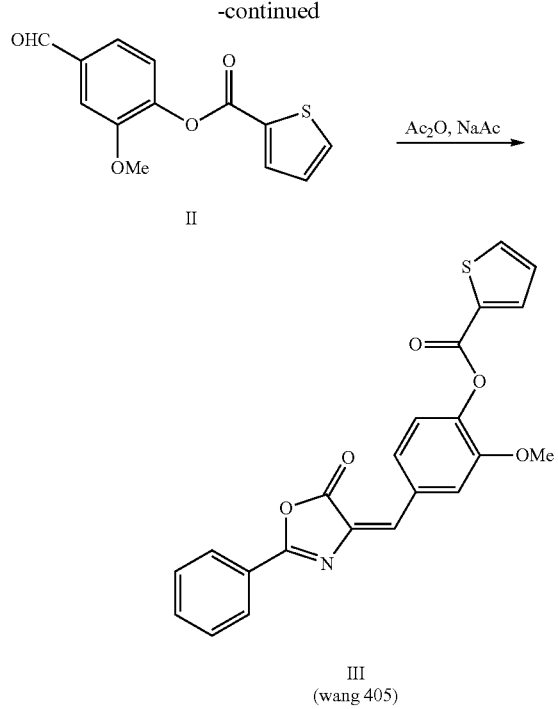

At room temperature, the compound II (262 mg, 1.0 mmol), the compound I (200 mg, 1.1 mmol), sodium acetate (82 mg, 1.0 mmol) and 1 mL of acetic anhydride are mixed and heated to 170° C. The reaction is maintained in the molten state for 1 hour. Then, 5 mL of ethanol is added into the resultant mixture, and then the reaction is cooled to room temperature. The yellow solids are separated out and filtered. The residual liquid is concentrated and the solvent is removed completely to obtain the crude product, which is isolated over silica gel column with petroleum ether/ethyl acetate (6:1 v/v) to obtain 235 mg of the compound wang405 (yield: 58%).

¹HNMR (300 MHz, CDCl₃) δ 3.97 (s, 3H), 7.21 (dd, J=4.8 Hz, 3.9 Hz, 1H), 7.24 (s, 1H), 7.26 (d, J=7.8 Hz, 1H), 7.51-7.57 (2H), 7.60-7.70 (3H), 8.02 (dd, J=3.6 Hz, 0.9 Hz, 1H), 8.14-8.19 (3H).

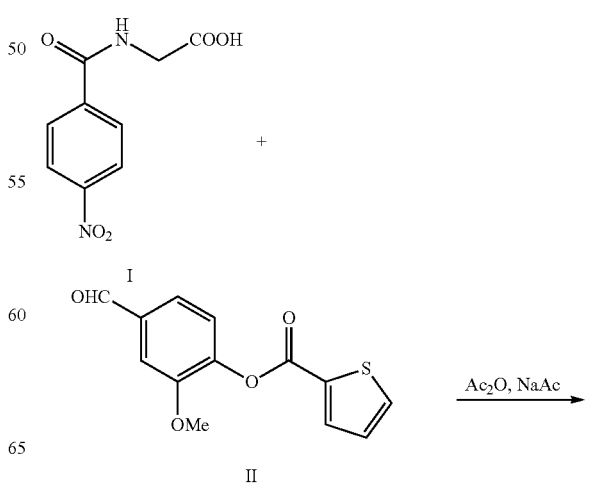

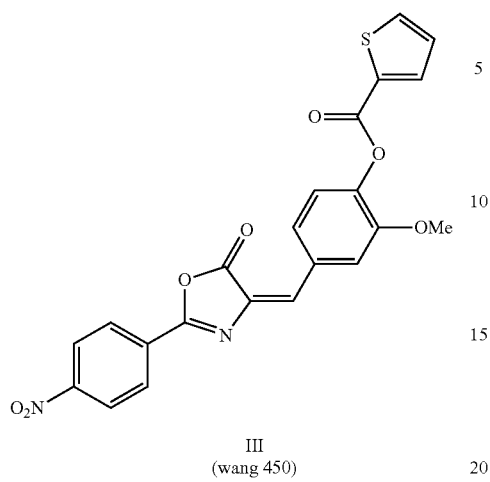

III
(wang 450)

At room temperature, the compound II (262 mg, 1.0 mmol), the compound I (250 mg, 1.1 mmol), sodium acetate (82 mg, 1.0 mmol) and 4 mL of acetic anhydride are mixed and heated to 210 to 230° C. The reaction is maintained in the molten state for 1 hour. Then, 5 mL of ethanol is added into the resultant mixture, and then the reaction is cooled to room temperature. The yellow solids are separated out and filtered to obtain 100 mg of the compound wang450 (yield: 22%).

$^1$HNMR (300 MHz, CDCl$_3$) δ 3.97 (s, 3H), 72.1 (dd, J=4.8 Hz, 3.9 Hz, 1H), 7.30 (d, J=8.1 Hz, 1H), 7.37 (s, 1H), 7.70 (d, J=5.1 Hz, 1H), 7.73 (dd, J=9.9 Hz, 1.5 Hz, 1H), 8.02 (d, J=3.9 Hz, 1H), 8.09 (d, J=1.8 Hz, 1H), 8.33 (d, J=9.0 Hz, 2H), 8.40 (d, 9.3 Hz, 2H).

EXAMPLE 2

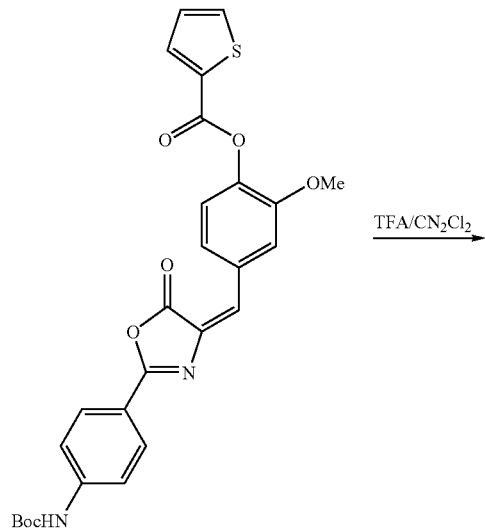

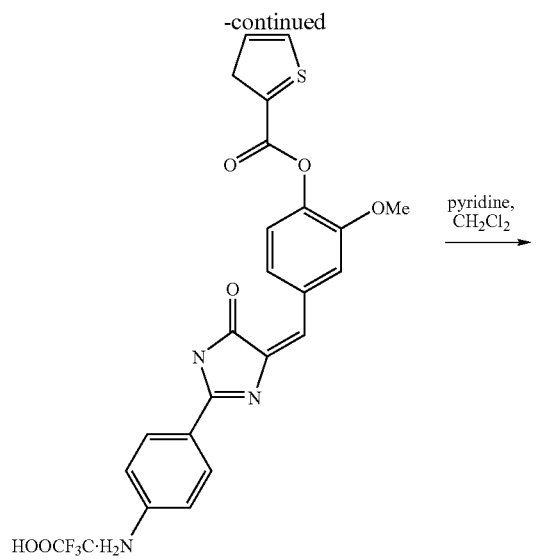

wang420

The compound I (50 mg, 0.1 mmol) is dissolved in 2 mL of dichloromethane, and cooled in the cryohydrate bath at −20° C., followed by 1 mL of trifluoroacetic acid. The reaction is stirred at room temperature and traced with TLC until the compound I is reacted completely. After concentrating the reaction system and removing trifluoroacetic acid completely, then the reaction intermediate is dissolved in 2 mL of dichloromethane, and cooled in the cryohydrate bath at −20°, followed by adding 40 μL (0.6 mmol) of pyridine The reaction is stirred at room temperature and traced with TLC. After concentration the crude product is obtained, which is isolated over silica gel column with petroleum ether/ethyl acetate (2:1 v/v) to obtain 38 mg of the compound wang420 (yield: 90%).

$^1$HNMR (300 MHz, CDCl$_3$) δ 3.94 (s, 3H), 7.20-7.24 (m, 2H), 7.27 (d, J=1.8 Hz, 1H), 7.66 (dd, J=8.1 Hz, 1.5 Hz, 1H), 7.71 (dd, J=4.8 Hz, 0.9 Hz, 1H), 7.76 (d, 9.0 Hz, 2H), 8.03 (dd, J=3.6 Hz, 0.9 Hz, 1H), 8.07 (d, J=1.5 Hz, 1H), 8.14 (d, J=8.7 Hz, 2H), 8.20 (br, 2H).

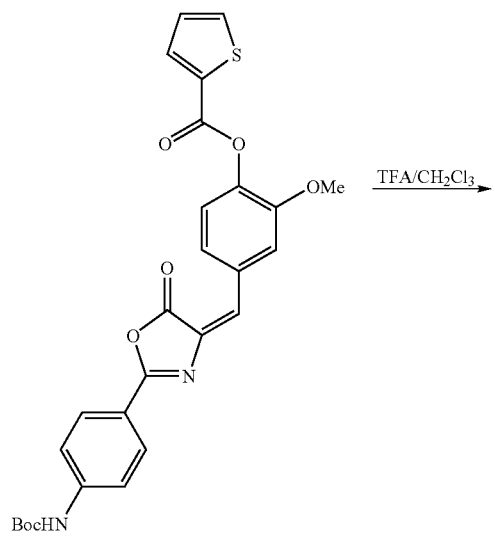
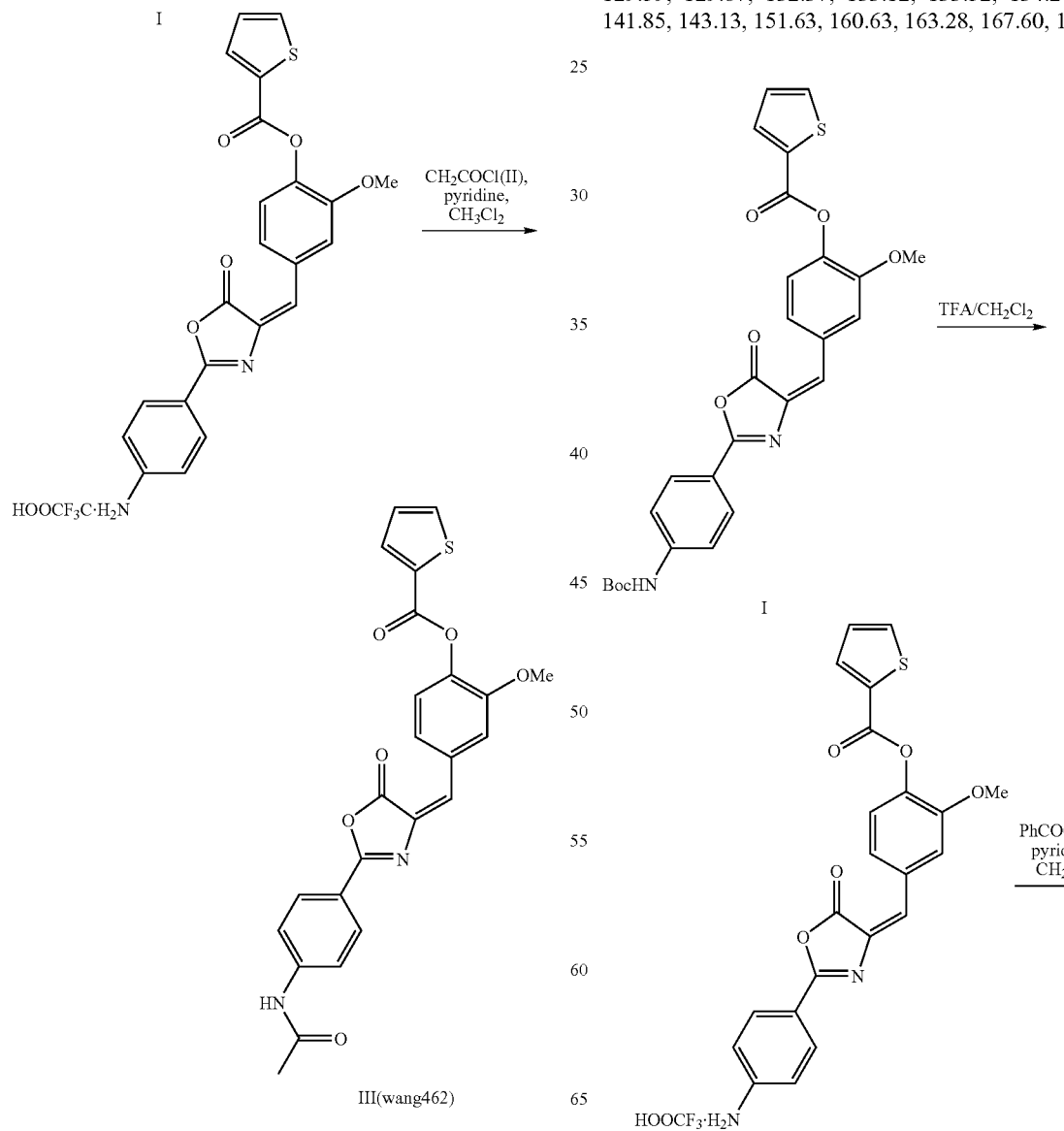

The compound I (50 mg, 0.1 mmol) is dissolved in 2 mL of dichloromethane, and cooled in the cryohydrate bath at −20° C., followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20°, followed by adding 40 μL (0.6 mmol) of pyridine and compound II (27 μL, 0.39 mmol). The reaction is stirred at room temperature and traced with TLC. After concentration the crude product is obtained, which is isolated over silica gel column with petroleum ether/ethyl acetate (1.5:1 v/v) to obtain 26 mg of the compound wang462 (yield: 56%).

$^1$H NMR (300 MHz, CDCl$_3$) δ 2.19 (s, 3H), 3.88 (s, 3H), 7.12 (s, 1H), 7.20-7.24 (m, 2H), 7.55 (d, J=1.5 Hz, 1H), 7.60 (d, 9.0 Hz, 2H), 7.71 (dd, J=4.8 Hz, 0.9 Hz, 1H), 7.77 (br, 1H), 7.97 (d, J=8.7 Hz, 2H), 8.03 (dd, J=3.9 Hz, 0.9 Hz, 1H), 8.07 (d, J=1.5 Hz, 1H); $^{13}$C NMR (75 MHz, CDCl$_3$) δ 24.66, 55.84, 155.64, 119.55, 120.54, 123.35, 126.15, 123.43, 129.59, 129.87, 132.37, 133.12, 133.52, 134.26, 135.41, 141.85, 143.13, 151.63, 160.63, 163.28, 167.60, 168.99.

-continued

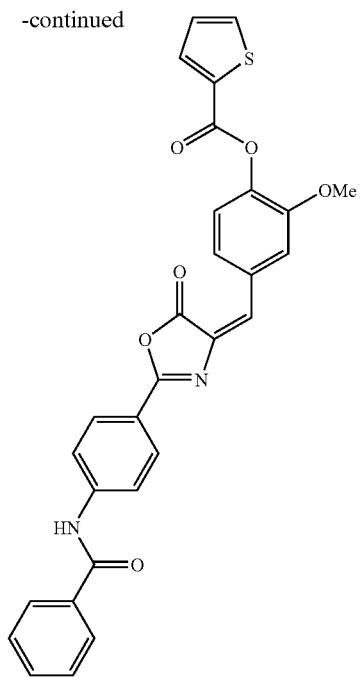

III (wang524)

The compound I (40 mg, 0.08 mmol) is dissolved in 2 mL of dichloromethane, and cooled in the cryohydrate bath at −20° C. followed by 1 mL of trifluoroacetic acid. The solution is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20°, followed by adding 40 μL (0.6 mmol) of pyridine and the compound II (23 μL, 0.2 mmol). The mixture is stirred at room temperature and traced with TLC. After concentration the crude product is obtained, which is isolated over silica gel column with petroleum ether/ethyl acetate (5:1 v/v) to obtain 15 mg of the compound wang524 (yield: 36%).

$^3$HNMR (300 MHz, DMSO-d$_6$) δ 3.90 (s, 3H), 7.22 (d, J=5.4 Hz, 1H), 7.33, (d, J=8.4 Hz, 2H), 7.39-7.44 (1H), 7.50-7.58 (2H), 7.83 (d, J=8.4 Hz), 7.98 (d, J=8.7 Hz, 2H), 8.04-8.22 (7H), 10.74 (s, 1H).

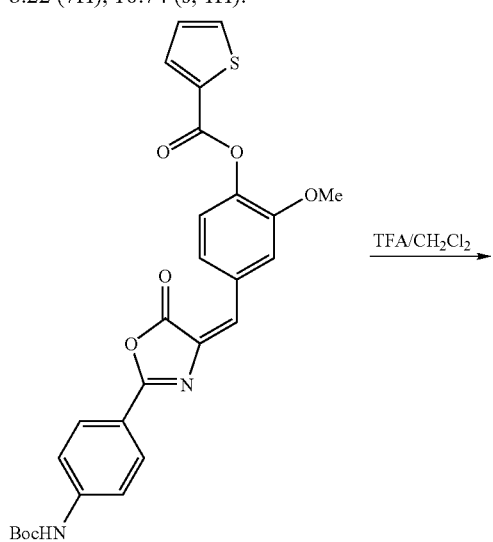

I

-continued

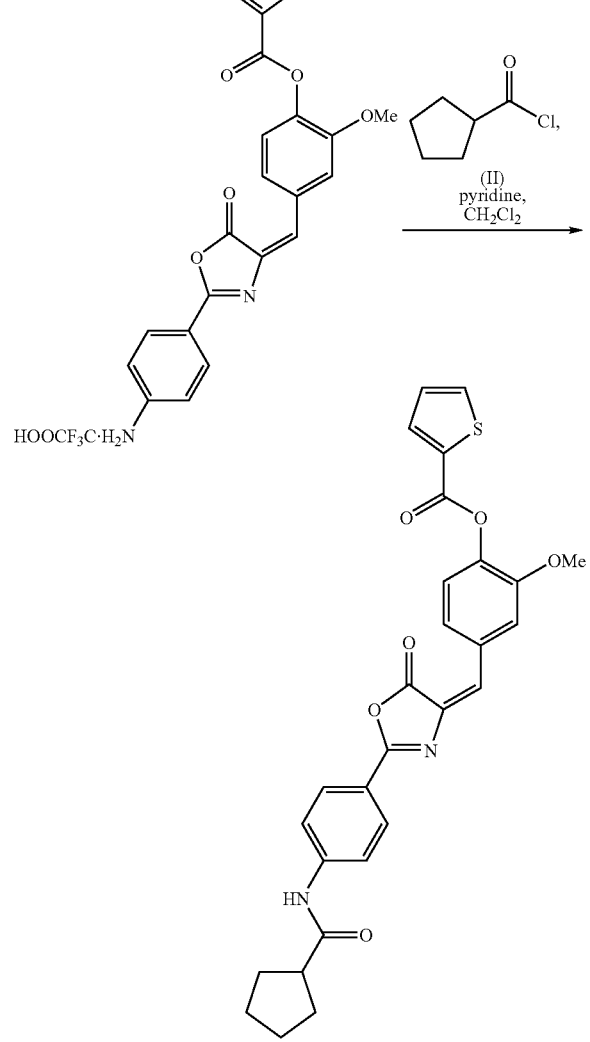

III(wang516)

The compound I (40 mg, 0.08 mmol) is dissolved in 2 mL of dichloromethane, and cooled in the cryohydrate bath at −20° C. followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20° followed by adding 40 μL (0.6 mmol) of pyridine and the compound II (25 μL, 0.2 mmol). The reaction is stirred at room temperature and traced with TLC. After concentration the crude product is obtained, which is isolated over silica gel column with petroleum ether/ethyl acetate (4:1 v/v) to obtain 25 mg of the compound wang516 (yield: 62.5%).

$^1$H NMR. (300 MHz, DMSO-d$_6$) δ 1.57 (m, 2H), 1.63-1.77 (m, 4H), 1.80-1.89 (m, 2H), 2.84 (m, 1H), 3.89 (s, 3H), 7.31 (m, 2H) 7.40 (d, J=8.4 Hz, 1H), 7.86 (d, J=9.0 Hz, 2H), 7.94 (dd, J=8.4 Hz, 1.8 Hz, 1H), 8.03 (dd, J=3.9 Hz, 1.2 Hz, 1H), 8.07 (d, J=9.0 Hz, 2H), 8.10 (dd, J=4.8 Hz, 1.2 Hz, 1H), 8.18 (d, J=1.8 Hz, 1H), 10.35 (s, 1H); $^{13}$C NMR (75 MHz, DMSO-d$_6$) δ 25.62, 30.00, 55.97, 115.74, 118.71, 119.04, 123.52, 125.27, 128.51, 128.77, 129.24, 131.19, 132.78, 133.34, 135.43, 135.50, 140.86, 144.42, 151.04, 159.24, 162.91, 166.93, 175.11.

The compound I (40 mg, 0.08 mmol) is dissolved in 2 mL of dichloromethane, and cooled in the cryohydrate bath at −20° C. followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20°, followed by adding 40 µL (0.6 mmol) of pyridine and the compound II (23 µL, 0.2 mmol). The reaction is stirred at room temperature and traced with TLC. After concentration the crude product is obtained, which is isolated over silica gel column with petroleum ether/ethyl acetate (4:1 v/v) to obtain 25 mg of the compound wang488 (yield: 64%).

$^1$H NMR (300 MHz, DMSO-$d_6$) δ 0.80 (m, 2H), 0.85 (m, 2H), 1.84 (m, 1H), 3.88 (s, 3H), 7.28 (s, 1H), 7.32 (dd, J=5.1 Hz, 3.9 Hz, 1H), 7.39 (d, J=8.1 Hz, 1H), 7.85 (d, J=8.7 Hz, 2H), 7.92 (dd, J=8.4 Hz, 1.5 Hz, 1H), 8.04 (m, 1H), 8.05 (J=8.7 Hz, 2H), 8.11 (dd, J=4.8 Hz, 1.2 Hz, 1H), 8.18 (d, J=1.8 Hz, 1H), 10.68 (s, 1H); $^{13}$C NMR (75 MHz, DMSO-$d_6$) δ 7.78, 14.83, 55.97, 115.71, 118.73, 118.93, 123.53, 125.32, 123.54, 128.81, 129.32, 131.22, 132.80, 133.36, 335.46, 135.53, 140.88, 144.24, 151.05, 159.29, 162.91, 166.96, 172.44.

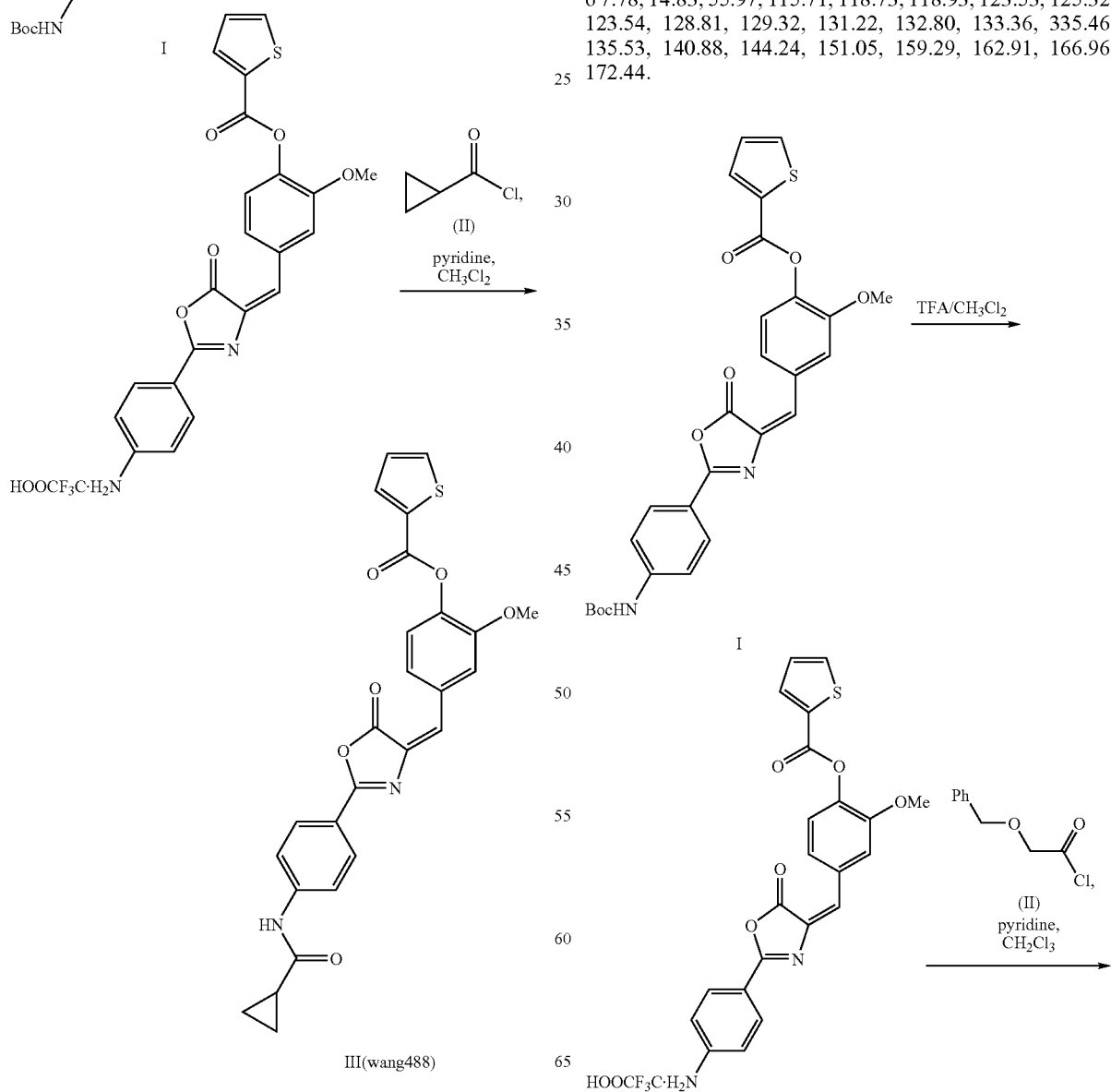

-continued

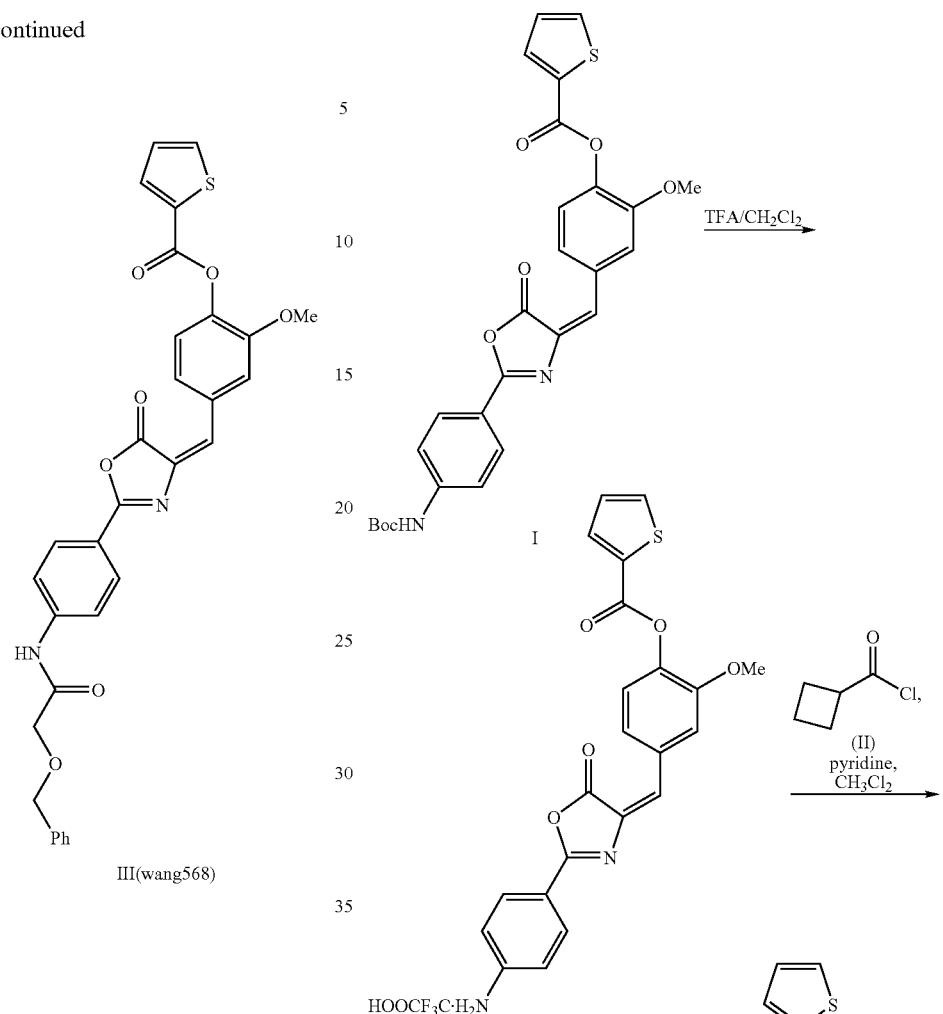

III(wang568)

III(wang502)

The compound I (40 mg, 0.08 mmol) is dissolved in 2 mL of dichloromethane, and cooled in the cryohydrate bath at −20° followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane and cooled in the cryohydrate bath at −20°, followed by adding 40 μL (0.6 mmol) of pyridine and the compound II (23 μL, 0.2 mmol). The reaction is stirred at room temperature and traced with TLC. After concentration the crude product is obtained, which is isolated over silica gel column with petroleum ether/ethyl acetate (4:1 v/v) to obtain 26 mg of the compound wang568 (yield: 57%).

$^1$H NMR (300 MHz CDCl$_3$) δ 3.95 (s, 3H), 4.13 (s, 2H), 4.68 (s, 2H), 7.18 (s, 1H), 7.19-7.26 (m, 2H), 7.39-7.50 (m, 5H), 7.63 (dd, J=6.9 Hz, 0.9 Hz, 1H), 7.69 (dd, J=4.8 Hz, 0.9 Hz, 1H), 7.74 (d, J=9.0 Hz, 2H), 8.01 (dd, J=3.6 Hz, 1.2 Hz, 1H), 8.10 (d, J=8.7 Hz, 2H), 8.16 (d, J=1.5 Hz, 1H), 8.56 (s, 1H).

The compound I (40 mg, 0.08 mmol) is dissolved in 2 mL of dichloromethane, and cooled in the cryohydrate bath at −20° followed by 1 mL of trifluoroacetic acid. The reaction is at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20° followed by adding 40 μL (0.6 mmol) of pyridine and compound II (23 μL, 0.2 mmol). The reaction is stirred at room temperature and traced with TLC. After concentration the crude product is obtained, which is isolated over silica gel column with petroleum ether/ ethyl acetate (4:1 v/v) to obtain 22 mg of product, the compound wang502 (yield: 56%).

$^1$H NMR (300 MHz, DMSO-$d_6$) δ 1.81-1.94 (m, 2H), 2.12-2.28 (m, 4H), 3.29 (m, 1H), 3.89 (s, 3H), 7.31 (s, 1H), 7.33 (m, 1H), 7.40 (d, J=7.5 Hz, 1H), 7.87 (d, J=8.1 Hz, 2H), 7.94 (d, J=8.1 Hz, 2H), 8.04-8.08 (2H), 8.12 (d, J=5.1 Hz, 1H), 8.19 (s, 1H), 10.20 (s, 1H).

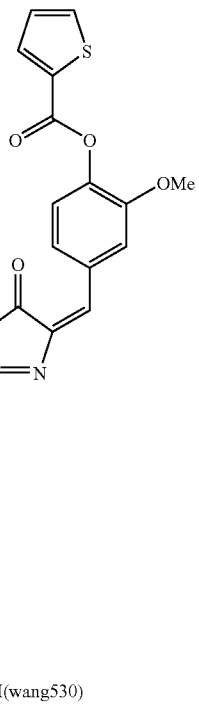

III(wang530)

The compound I (40 mg, 0.08 mmol) is dissolved in 2 mL of dichloromethane, and cooled in the cryohydrate bath at −20° followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20° followed by adding 40 μL (0.6 mmol) of pyridine and the compound II (23 μL, 0.2 mmol). The reaction is stirred at room temperature and traced with TLC. After concentration the crude product is obtained, which is isolated over silica gel column with petroleum ether/ethyl acetate (4:1 v/v) to obtain 24 mg of the compound wang530 (yield: 57%).

$^1$H NMR (300 MHz, DMSO-$d_6$) δ 1.20-1.48 (6H), 1.65-1.81 (4H), 2.39 (m, 1H), 3.89 (s, 3H) 7.32 (s, 1H), 7.34 (m, 1H), 7.41 (d, J=8.4 Hz, 1H), 7.87 (d, J=8.1 Hz, 2H), 7.95 (d, J=8.1 Hz, 1H), 8.04 (m, 1H), 8.08 (d, J=8.7 Hz, 2H), 8.12 (d, J=4.8 Hz, 1H), 8.20 (m, 1H), 10.31 (s, 1H).

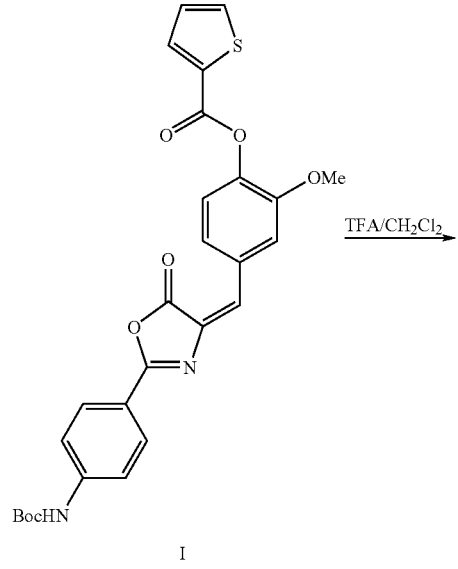

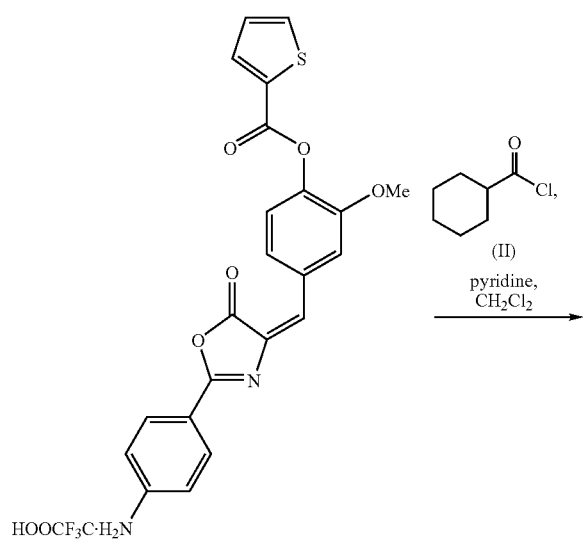

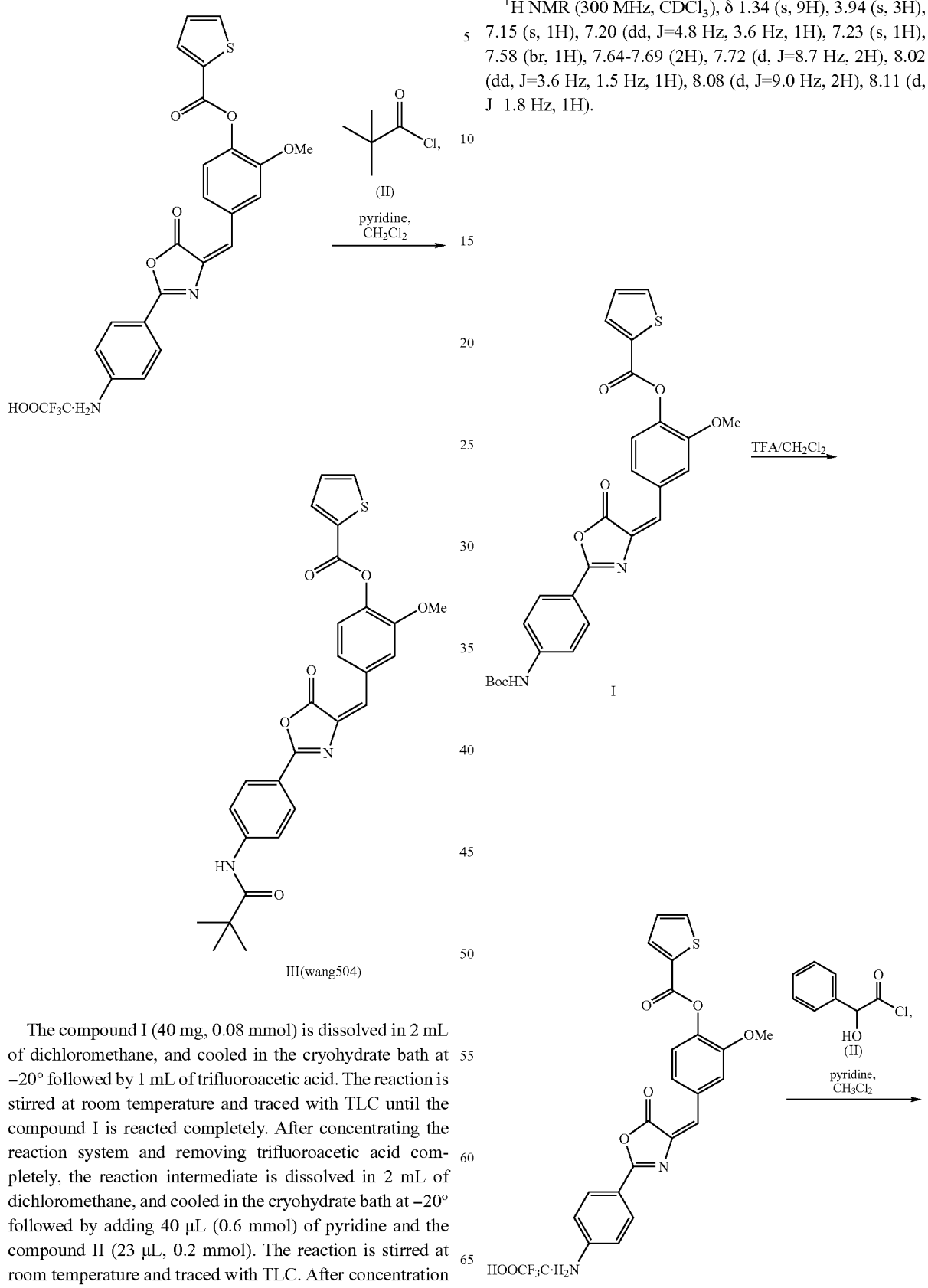

column with petroleum ether/ethyl acetate (6:1 v/v) to obtain 4 mg of the compound wang504 (yield: 10%).

$^1$H NMR (300 MHz, CDCl$_3$), δ 1.34 (s, 9H), 3.94 (s, 3H), 7.15 (s, 1H), 7.20 (dd, J=4.8 Hz, 3.6 Hz, 1H), 7.23 (s, 1H), 7.58 (br, 1H), 7.64-7.69 (2H), 7.72 (d, J=8.7 Hz, 2H), 8.02 (dd, J=3.6 Hz, 1.5 Hz, 1H), 8.08 (d, J=9.0 Hz, 2H), 8.11 (d, J=1.8 Hz, 1H).

The compound I (40 mg, 0.08 mmol) is dissolved in 2 mL of dichloromethane, and cooled in the cryohydrate bath at −20° followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20° followed by adding 40 μL (0.6 mmol) of pyridine and the compound II (23 μL, 0.2 mmol). The reaction is stirred at room temperature and traced with TLC. After concentration the crude product is obtained, which is isolated over silica gel

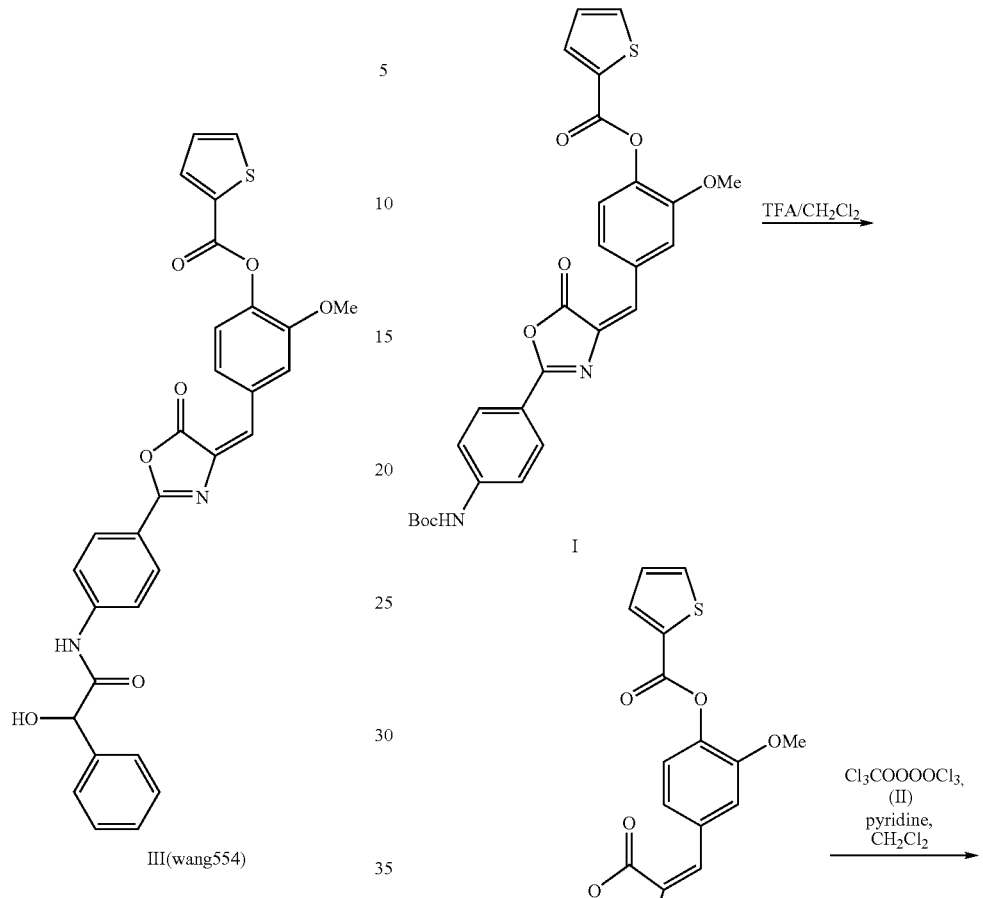

III(wang554)

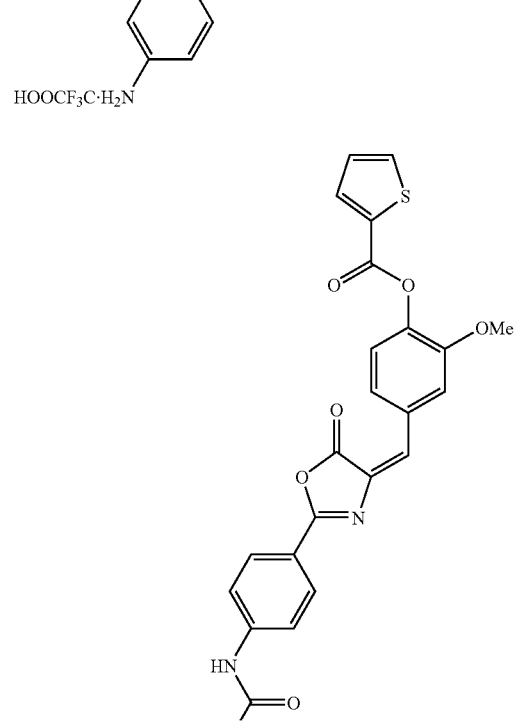

The compound I (40 mg, 0.08 mmol) is dissolved in 2 mL of dichloromethane and cooled in the cryohydrate bath at −20° followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20°, followed by adding 40 μL (0.6 mmol) of pyridine and the compound II (27 μL, 0.2 mmol). The reaction is stirred at room temperature and traced with TLC. After concentration the crude product is obtained, which is isolated over silica gel column with $CH_2Cl_2$ to obtain 40 mg of the compound wang554 (yield: 89%).

$^1$H NMR (300 MHz, $CDCl_3$) δ 3.83 (s, 3H), 6.28 (s, 1H), 7.05 (s, 1H), 7.16 (d, J=8.1 Hz, 1H), 7.20 (dd, J=5.1 Hz, 3.6 Hz, 1H), 7.39-7.41 (2H), 7.50-7.55 (3H), 7.60 (d, J=9.0 Hz, 2H), 7.71 (dd, J=5.1 Hz, 1.2 Hz, 1H), 7.92 (d, J=8.4 Hz, 2H), 7.99 (d, J=1.2 Hz), 8.03 (dd, J=3.6 Hz, 0.9 Hz, 2H), 8.24 (s, 1H), 8.42 (s, 1H).

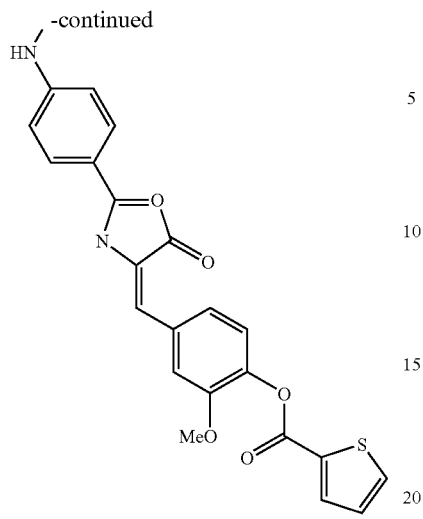

III(wang866)

The compound I (52 mg, 0.1 mmol) is dissolved in 2 mL of dichloromethane and cooled in the cryohydrate bath at followed by 1 mL of trifluoroacetic acid. The reaction is stirred at room temperature and traced with TLC until the compound I is reacted completely. After concentrating the reaction system and removing trifluoroacetic acid completely, the reaction intermediate is dissolved in 2 mL of dichloromethane, and cooled in the cryohydrate bath at −20°, followed by adding 40 μL (0.6 mmol) of pyridine and the compound II (10 mg, 0.03 mmol). The solution is stirred at room temperature and traced with TLC. After concentration the crude product is obtained, which is isolated over silica gel column with CH$_2$Cl$_2$ to obtain 19 mg of the compound wang866 (yield: 44%).

$^1$H NMR (300 MHz, DMSO-d$_6$) δ 3.89 (s, 6H), 7.33 (dd, J=4.8 Hz, 3.9 Hz, 2H) 7.36 (s, 2H), 7.41 (d, J=8.4 Hz, 2H), 7.93-7.96 (2H), 7.96 (d, J=8.7 Hz, 4H), 8.04 (dd, 3.3 Hz, 0.9 Hz, 2H), 8.12 (dd, J=4.8 Hz, 0.9 Hz, 2H), 8.17 (d, J=8.7 Hz, 4H), 8.20 (d, J=1.8 Hz, 2H), 11.66 (s, 2H).

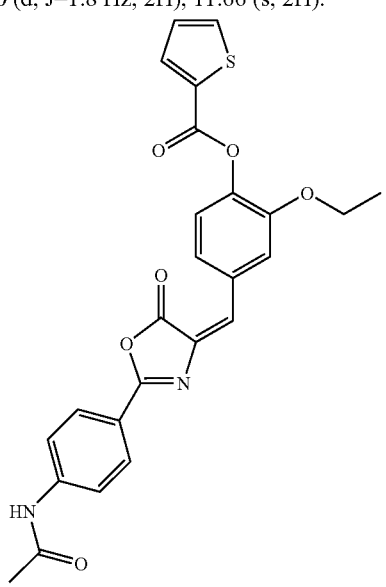

2f

According to the same procedure, the compound 2f is prepared in 56% yield from 1 eq of compound

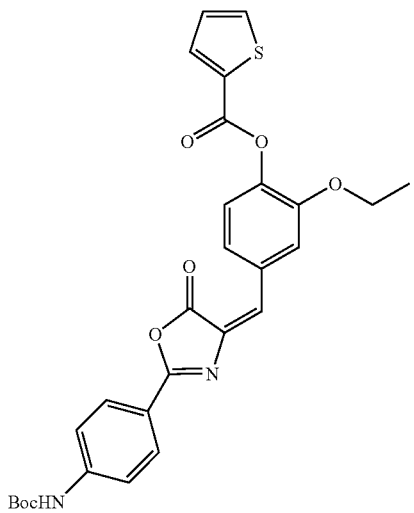

and 1.5 eq of acetyl chloride.

$^1$H NMR (300 MHz, CDCl$_3$) δ 1.41 (t, J=6.9 Hz, 3H), 2.24 (s, 3H), 4.18 (q, J=6.9 Hz, 2H) 7.11 (s, 1H), 7.19 (m, 1H), 7.45 (m, 2H), 7.62-7.70 (4H), 8.02 (m, 1H), 8.08 (d, J=9.0 Hz, 2H).

wang582

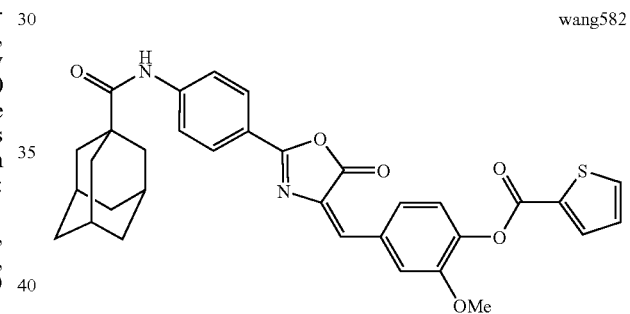

According to the same procedure, the compound wang582 is prepared in 38% yield from 1 eq of the compound wang520 and 1.5 eq of diamantane formyl chloride.

$^1$NMR (300 MHz, CDCl$_3$) δ 1.76 (6H), 1.99 (6H), 2.12 (3H), 3.95 (s, 3H), 7.14-7.23 (2H), 7.54 (s, 1H), 7.61-7.70 (2H), 7.73 (d, J=9.0 Hz, 2H), 8.02 (dd, J=3.9 Hz, 1H), 8.09 (d, J=9.0 Hz, 2H), 8.12 (d, J=1.8 Hz, 1H).

wang538

According the same procedure, the compound wang538 is prepared in 58% yield from 1 eq of the compound wang520 and 1.5 eq of benzyl acetyl chloride.

¹H NMR (300 MHz, CDCl₃) δ 3.78 (s, 2H), 3.92 (s, 3H), 7.16 (s, 1H), 7.19-7.24 (2H), 7.34-7.74 (6H), 7.59 (d, J=8.7 Hz, 2H), 7.62 (m, 1H), 7.70 (d, J=4.8 Hz, 1H), 8.02 (d, J=8.7 Hz, 2H), 8.13 (m, 1H).

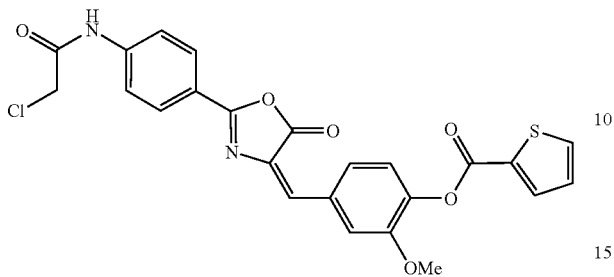

wang496

According the same procedure, the compound wang496 is prepared in 70% yield from 1 eg of the compound wang520 and 1.5 eq of chloro acetyl chloride.

¹H NMR (300 MHz, DMSO-d₆) δ 3.89 (s, 3H), 4.36 (s, 2H), 7.34 (s, 1H), 7.41 (d, J=8.1 Hz, 1H), 7.88 (d, J=9.0 Hz, 2H), 7.93-7.98 (2H), 8.05 (m, 1H), 8.12 (d, J=7.5 Hz, 2H), 8.22 (m, 1H), 8.89 (m, 1H), 10.95 (s, 1H).

EXAMPLE 3

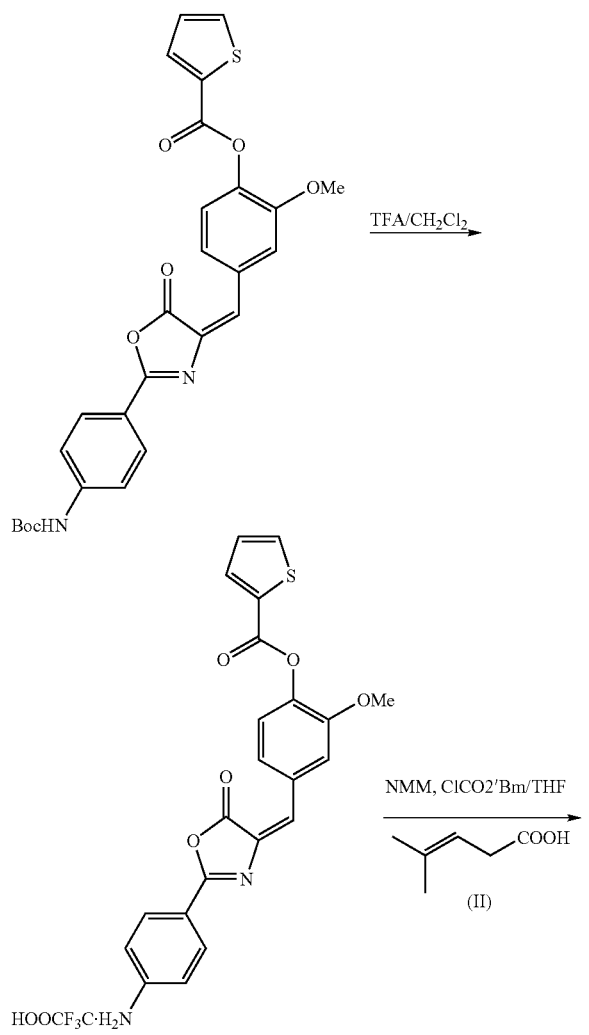

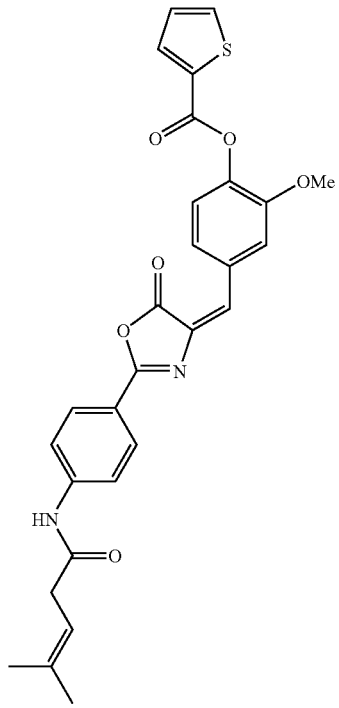

III(wang516-1)

The compound I (40 mg, 0.08 mmol) is dissolved in 2 mL of dichloromethane, and cooled in the cryohydrate bath at −20° followed by 1 mL of trifluoroacetic acid. The reaction is stirred at room temperature and traced with TLC until the compound I is reacted completely. The solution is concentrated and trifluoroacetic acid is removed completely. In another dry 10 mL round-bottomed flask, the compound II (19 μL, 0.16 mmol) is dissolved in 2 mL of tetrahydrofuran, and cooled in the cryohydrate bath at −20° with stirring for 10 min at this temperature. Then, N-methylmorpholine (NMM) (53 μL, 0.48 mmol) and ClCOO$^i$Bu (21 μL, 0.16 mmol) are added orderly with stirring for 0.5 hour at −20°. The residue of the compound I with trifluoroacetic acid is dissolved in 1 mL of tetrahydrofuran and then transferred into the above mixture with the syringe so as to react at the room temperature for about 15 hours. After concentration the crude product is obtained, which is isolated over silica gel column with petroleum ether/ethyl acetate (5:1 v/v) to obtain 12 mg of the compound wang516-1(yield: 30%).

¹H NMR (300 MHz, CDCl₃) δ 1.74 (s, 3H), 1.87 (s, 3H), 3.18 (d, J=7.8 Hz, 2H), 3.95 (s, 3H), 5.42 (m, 1H), 7.19 (s, 1H), 7.20-7.27 (2H), 7.63 (2H), 7.65 (d, J=1.8 Hz, 1H), 7.70 (d, J=8.4 Hz, 2H), 8.02 (dd, J=3.6 Hz, 0.9 Hz, 1H), 8.09 (d, J=9.0 Hz, 2H), 8.16 (d, J=2.1 Hz, 1H).

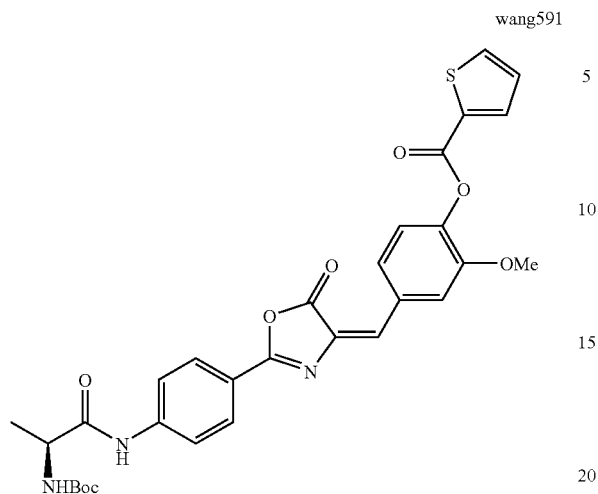
According to the same procedure, the compound wang591 is prepared in 18% yield from 1 eq of the compound wang520 and 2.0 eq of the compound Boc-Ala-OH.
EXAMPLE 4
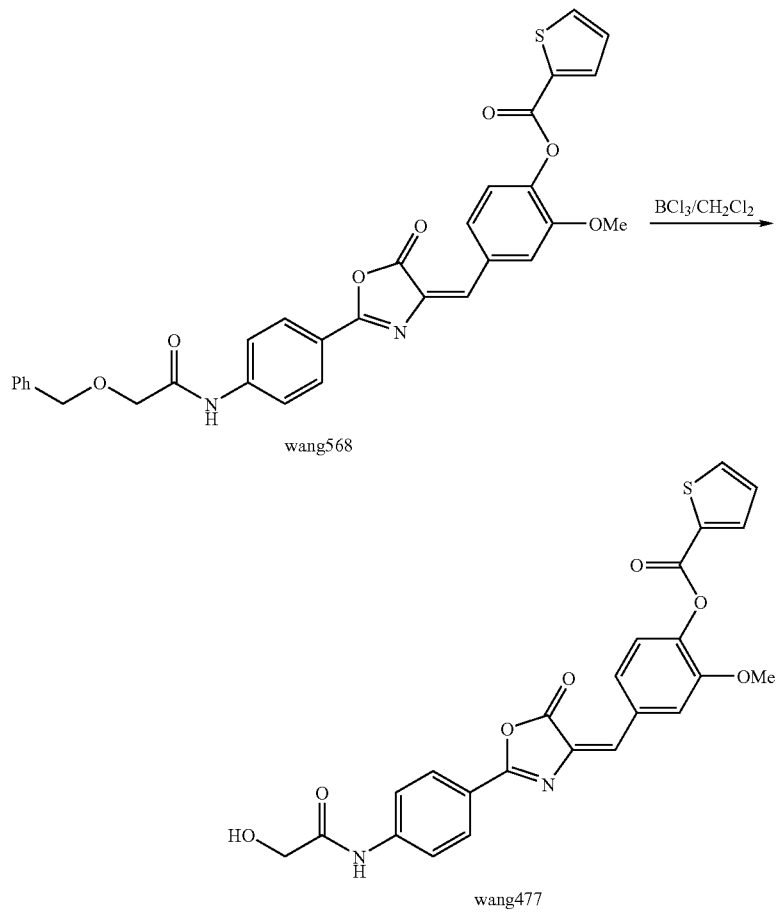

The compound wang568 (11 mg, 0.02 mmol) is dissolved in 2 mL of dichloromethane and cooled at −78° for 10 minutes, followed by 0.2 mL 1M of $BCl_3$ in n-hexane solution to continue stirring for 30 minutes at −78°. Then, the temperature is raised to −18° to react for 4 hours. 2 mL of ether is added to quench the reaction with stirring for 30 minutes at the room temperature, followed by adding 5 mL of water. The water phase and the organic phase are separated. The water phase is extracted with dichloromethane. The organic phase is combined and dried with anhydrous $MgSO_4$After concentration the crude product is obtained, which is isolated over column chromatography with petroleum ether/ethyl acetate (1/2, v/v) to obtain the compound wang477 (1.5 mg, yield: 17%).

$^1$H NMR (300 MHz, $CDCl_3$) δ 1.86 (br, 1H), 3.95 (s, 3H), 4.26 (s, 2H), 7.18 (s, 1H), 7.20 (dd, J=8.7 Hz, 4.8 Hz, 1H), 7.23 (d, J=3.3 Hz, 1H), 7.63 (d, J=8.1 Hz, 1H), 7.71 (dd, J=5.1 Hz, 1.5 Hz, 1H), 7.75 (d, J=8.7 Hz, 2H), 8.02 (d, J=3.6 Hz, 1H), 8.08 (d, J=8.7 Hz, 2H), 8.14 (m, 1H), 8.57 (br, 1H).

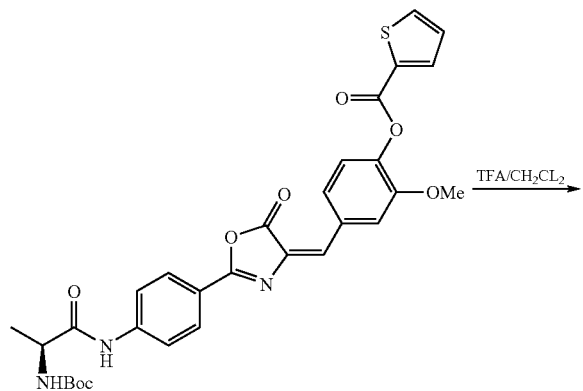

wang591

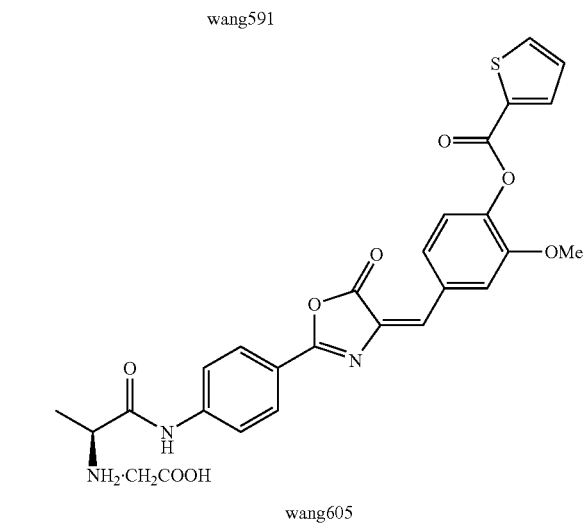

wang605

The compound wang591 (3 mg) is dissolved in 1.5 mL of dichloromethane, and cooled in ice bath for 5 minutes followed by 0.15 mL of trifluoroacetic acid. Then, the temperature is gradually raised to the room temperature, and the reaction is traced with TLC. After the raw material disappears, the solvent and trifluoroacetic acid are removed in vacuum to obtain 2 mg of the compound wang605 (yield: 65%).

$^3$H NMR (300 MHz, Methyl-$d_3$ Alcohol-d) δ 1.63 (d, J=7.2 Hz, 3H, 3.95 (s, 3H), 4.09 (m, 1H), 7.265 (s, 1H), 7.267 (d, J=8.7 Hz, 1H), 7.29 (d, J=8.1 Hz, 1H), 7.81 (dd, J=8.7 Hz, 2.1 Hz, 1H), 7.87 (d, J=9.0 Hz, 2H), 7.91 (dd, J=5.1 Hz, 1.2 Hz, 1H), 8.01 (dd, 3.6 Hz, 0.9 Hz, 1H), 8.16 (d, J=9.3 Hz, 2H), 8.25 (d, J=2.1 Hz, 1H).

EXAMPLE 5

Experimental Test on Biological Activity

1. Testing the Expression of the Report Gene

Upon that GLP-1R binds to GLP-1 or agonists, its Gα subunit is activated to stimulate the adenylate cyclase, which makes the increase in the concentration of intracellular cAMP. Since the promoter region of the proinsulin gene has the cAMP response element, upon binding of cAMP to this response element, the transcription of the proinsulin gene is activated, so as to increase the sensitivity of β-islet cells to glucose and improve the expression and secretion of insulin (Diabetes, 2000, vol.49: 1156-1164). The screening model employs the human embryonal nephric cell strain which is stably transfected with the expression vector of GLP-1R gene and the expression vector of luciferase report gene under the regulation of cAMP response element, to detect its response to the candidate compound (Cell Biology, 1992, Vol.89: 8641-8645; Proc. Natl. Acad. Sci. U.S.A. 1987, Vol.84: 3434-3438). When screening the candidate compounds, the compounds which may induce the luciferase report gene to express have the activity of activating GLP-1.

1.1 Experimental Material and Instruments

Cell strain: HEK 293/GLP1R+Luc strain which stably express GLP-1R and luciferase (National New Medicaments Screening Center)

Fetal calf serum (GIBCO/BRL Cooperation)

Steady-glo™ luciferase analysis system (Promega Cooperation)

Standard GLP-1 (Sigma Cooperation)

G418 (Invitrogen Cooperation)

Forma carbon dioxide incubator (Forma Cooperation)

Victor 2 counting machine (Wallac Cooperation)

Candidate compound: the compounds wang524, wang520, wang462, 2f, wang516, wang516-2, wang502 and wang504;

1.2 Experimental process

HEK 293/GLP1R+Luc cell in 20000 cells/100 μl/well are inoculated into 96-well plate, cultured at 37° overnight with DMEM culture medium containing 10% of fetal calf serum and 500 μg/mL of G418. The candidate compounds wang516-2, wang502, and wang504 are respectively diluted to 2 mM, 1 mM, 0.3 mM, 0.1 mM, 0.03 mM, 0.01 mM, and 0.003 mM, and the other candidate compounds are diluted gradually from 30mM for 8 times by a ratio of 1:3 to get a concentration gradient (i.e., 30 mM, 10 mM, 3 mM, 1 mM, 0.3 mM, 0.1 mM, 0.03 mM, and 0.01 mM), which is added into the above 96-well plate at 1 μl/well. Then, the cells are cultured at 37 in 5% of $CO_2$ for 6 hours. The activity of luciferase is detected according to the specification of Steady-glo™ luciferase analysis system kit, and counting is performed with Victor 2 counting machine. The positive control adopts 30nM of standard GLP-1.

1.3 Experimental Result

The experimental result of the report gene for the candidate compounds is as shown in FIG. 1 and Table 1.

FIG. 1 shows that the compound wang 520 in a final concentration of 30 μM has the best relative activity (94%) which is improved greatly compared with that of the compound 2f. In addition, the compounds as shown in Table 1 have the dose dependency on the activity of GLP-1 R, wherein the $EC_{50}$ of the compounds of wang520, wang516. wang554, wang488, wang516-2, wang502 and wang504 are less than 10 μM. Such result provides the direction for determining the superior structure of the interaction of the compounds with GLP-1 R.

TABLE 1

| ID | $EC_{50}/\mu M$ |
|---|---|
| wang524 | 46.5 |
| wang520 | 4.6 |
| wang462 | 11.6 |
| wang516 | 6.85 |
| 2f | 13.0 |
| wang866 | 54.41 |
| wang554 | 5.24 |
| wang488 | 6.73 |
| wang516-2 | 6.06 |
| wang502 | 3.31 |
| wang504 | 4.87 |

2. Determination of the Concentration of Intracellular cAMP

Since the determination of the concentration of intracellular cAMP indirectly by detecting the expression of the report gene is an indirect process, the functional re-screen is directly performed with the cAMP-detecting kit in order to make sure that the compound can surely increase the concentration of intracellular cAMP.

2.1 Experimental Material and Instruments cAMP-detecting kit (Applied Biosystems Cooperation)

Forma carbon dioxide incubator (Forma Cooperation)

Victor 2 according machine (Wallac Cooperation)

HEK 293/GLP1 R+Luc strain which stably express GLP-1 R and luciferase (National new medicaments screening center)

Candidate compound: the compound 2f

Standard cAMP (provided in the kit, Applied Biosystems Cooperation)

2.2 Experimental process

HEK 293 cells are inoculated into 96-well plate in 20000 cells/100 μl/well, which is cultured at 37° overnight. The compound 2f is diluted to 1.00E-03M, 1.00E-04M, 1.00E-05M, 1.00E-06M and 1.00E-07M with dimethyl sulphoxide, followed by being inoculated into the above 96-well plate in 1l/well and being cultured at 37 with 5% of $CO_2$ for 1 hour. The concentration of intracellular cAMP is detected according to the specification of cAMP-Screen Direct TM system kit.

2.3 Experimental Result

Figure 2:
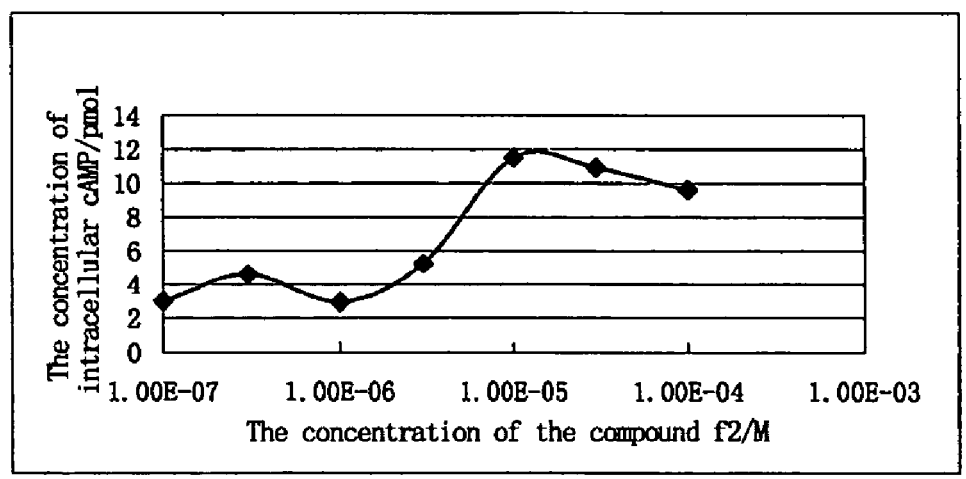
FIG. 2 shows the affection of the compound 2f on the concentration of cAMP in 293/GLP-1 R cells.

The final result of the concentration of intracellular cAMP is shown in FIG. 2. As shown in FIG. 2, with the increase of the concentration of the compound 2f, the concentration of cAMP which is produced under this stimulation shows an exponential increase. This indicates that the compound 2f has a certain effect on signal transmission of GLP-1 R as a GLP-1 R agonist. When the concentration of the compound 2f increases to 30 μM and 100 μM, the concentration of cAMP shows the decreasing trend, which is caused by the cellulotoxic effect of the high concentration of the compound 2f.

3. The Test on the Ligand-Binding Activity

In order to determine the binding activities of the compounds, the cells which highly express GLP-1 R are prepared, GLP-1 labelled with $^{125}I$ is used as the ligand, while adding into the candidate compound. When the candidate compound binds the $^{125}I$-labelled GLP-1 competitively, the isotope labels on the cell membrane reduce. Accordingly, the affinity of the candidate compound to the ligand can be evaluated (J Mol Endocrinol. 2000 Vol.25:321-35; J Biomol Screen, 2000 Vol. 5:377-84).

3.1 Experimental Material and Instruments

HEK 293/GLP1R+Luc cell strain (National New Medicaments Screening Center)

Labeled compound: $^{125}I$-labelled GLP-1 (Amersham Biosciences Cooperation)

Wallac MicroBata work station (Perkin Elmer Cooperation)

TomTech cell collector (TomTec Cooperation)

The testing buffer solution:

20 mM of tris-HCl (pH 7.4) (Shanghai Shenggong biological engineering technology LTD), 100 mM of NaCl (Shanghai Chemical agents Cooperation), 15 mM of NaF (Shanghai Chemical agents Cooperation), 2 mM of deoxypyridoxine (Sigma Cooperation), 0.2 mM of phenylmethylsulfonyl fluoride (Sigma Cooperation), aprotinin (Shanghai Chemical agents Cooperation) (1 μg/ml), and leupeptin (Shanghai Chemical agents Cooperation) (1 μg/ml).

The washing solution:

20 mM of tris-HCl (pH 7.4), 100 mM of NaCl, and 15 mM NaF

The scintillation liquid (Wallac Cooperation)

The candidate compound is diluted with dimethyl sulphoxide at the concentration gradient of 0.1 nM, 1 nM, 10 nM, 100 nM, 1000 nM, 10,000 nM, and 100,000 nM.

3.2 Experimental Process $10^5$ HEK 293/GLP1R+Luc cells in the logarithmic growth phase are incubated together with the $^{125}I$-labelled GLP-1 positive peptide (the final concentration of 40 pM) in 200 μl of the testing buffer solution at 25 for 4 hours, while adding into the non-labeled positive peptide or the candidate compound. The cells are collected with the cell collector, followed by washing three times with the washing solution. The scintillation liquid is added into them, and each well is counted with Microbata counter.

3.3 Experimental Result

The result of the receptor-binding experiment is shown in Table 3. As shown in Table 3, the compound 2f has the better affinity to GLP-1R, but the affinities of compounds wang520 and wang516 are little weak, and other compounds substantially don't bind to the receptor in the testing concentration range.

TABLE 3

| ID | $EC_{50}/\mu M$ |
|---|---|
| wang524 | >100 μM |
| wang450 | >100 μM |
| wang405 | >100 μM |
| wang327 | >100 μM |
| wang520 | 60-100 μM |
| wang462 | >100 μM |
| wang866 | >100 μM |
| wang516 | 40-80 μM |
| wang420 | >100 μM |
| 2f | 31 μM |

What is claimed is:

1. A glucagon-like peptide-1 receptor agonist having the following structural formula:

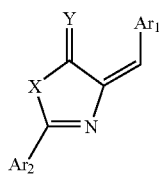

wherein $Ar_1$ is

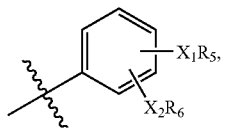

wherein $R_5$ is alkyl; $R_6$ thenoyl; $X_1$ is O; $X_2$ is O, wherein $Ar_2$ is

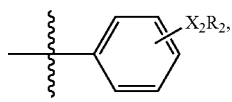

wherein $R_2$ is any one of the following substituent groups: alkanoyl; substituted alkanoyl which contains substituent groups including halogen, alkoxyl or hydroxyl; $C_2$-$C_6$ enoyl; $C_3$-$C_6$ cycloalkanoyl; benzoyl; substituted benzoyl which contains one, two or three substituent groups including alkoxyl and alkylamino; tert-butoxycarbonyl; adamantane formoxyl; and mandeloyl; and $X_2$ is NH;

X is O; and

Y is O.

2. The glucagon-like peptide-1 receptor agonist according to the claim 1 having the following structural formula:

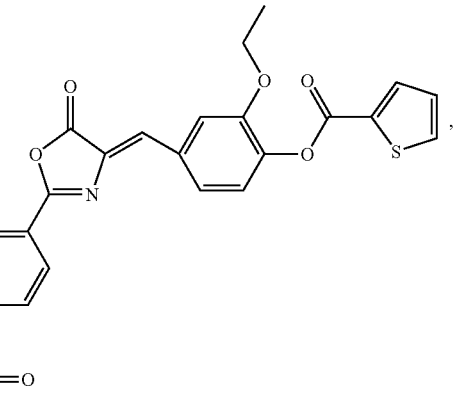,

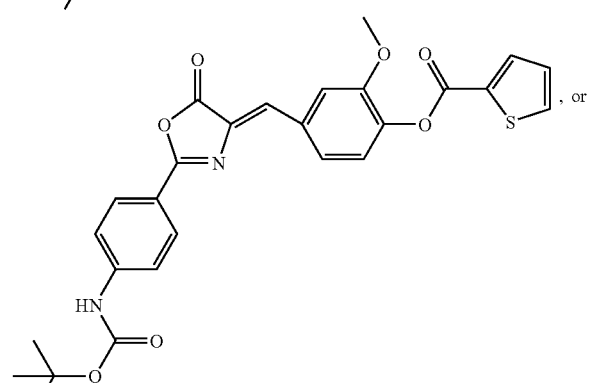, or

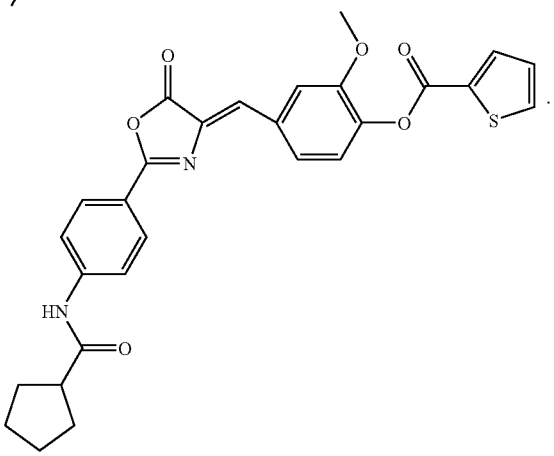.

* * * * *